US008968700B2

(12) United States Patent
Bogyo et al.

(10) Patent No.: US 8,968,700 B2
(45) Date of Patent: Mar. 3, 2015

(54) IMAGING OF PROTEASE ACTIVITY IN LIVE CELLS USING ACTIVITY BASED PROBES

(75) Inventors: Matthew S. Bogyo, Redwood City, CA (US); Galia Blum, Palo Alto, CA (US); Georges von Degenfeld, Leverkusen (DE)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 2171 days.

(21) Appl. No.: 11/502,255

(22) Filed: Aug. 10, 2006

(65) Prior Publication Data

US 2007/0036725 A1 Feb. 15, 2007

Related U.S. Application Data

(60) Provisional application No. 60/707,249, filed on Aug. 11, 2005.

(51) Int. Cl.
*A61K 51/00* (2006.01)
*A61M 36/14* (2006.01)
*C07K 1/107* (2006.01)
*A61K 49/00* (2006.01)
*C07K 5/065* (2006.01)

(52) U.S. Cl.
CPC ............ *C07K 1/1077* (2013.01); *A61K 49/0021* (2013.01); *A61K 49/0023* (2013.01); *A61K 49/0032* (2013.01); *A61K 49/0041* (2013.01); *A61K 49/0043* (2013.01); *A61K 49/0056* (2013.01); *C07K 5/06078* (2013.01)
USPC ........... 424/1.69; 424/1.11; 424/1.65; 424/9.6

(58) Field of Classification Search
CPC ......... A61K 9/00; A61K 31/00; A61K 38/00; A61K 38/02; A61K 38/03; A61K 39/00; A61K 49/00; A61K 49/001; A61K 49/0013; A61K 49/0017; A61K 49/0019; A61K 49/0021; A61K 49/0023; A61K 49/0026; A61K 49/0028; A61K 49/003; A61K 49/0032; A61K 49/0034; A61K 49/0036; A61K 49/0039; A61K 49/0041; A61K 49/0043; A61K 49/0045; A61K 49/0047; A61K 49/005; A61K 2121/00; A61K 2123/00; A61K 51/00; A61K 51/02; A61K 49/0056; A61K 5/00; C07K 5/04; C07K 1/1077; C07K 5/06078
USPC ........... 424/1.11, 1.65, 1.69, 1.81, 1.85, 1.89, 424/9.1, 9.6; 530/300, 331, 409
See application file for complete search history.

(56) References Cited

U.S. PATENT DOCUMENTS

| | | | |
|---|---|---|---|
| 5,936,731 A | 8/1999 | Cabib et al. | |
| 5,989,823 A | 11/1999 | Jayasena et al. | |
| 6,399,392 B1 | 6/2002 | Haugland et al. | |
| 6,690,817 B1 | 2/2004 | Cabib et al. | |
| 6,777,403 B2 | 8/2004 | Cheronis | |
| 2004/0018561 A1* | 1/2004 | DeCrescenzo et al. | 435/7.1 |
| 2004/0241679 A1 | 12/2004 | Lee | |
| 2005/0014160 A1 | 1/2005 | Kumaraswamy et al. | |

FOREIGN PATENT DOCUMENTS

WO    WO 01/86001    11/2001

OTHER PUBLICATIONS

Bio-Synthesis, Fluorescence and Quencher FRET Peptides, 1984, http://www.biosyn.com/faq/Fluorescence-and-Quencher-FRET-Peptides.aspx.*
Life Technologies-Invitrogen, The Molecular Probes Handbook, 2010, Fluorophores and Their Amine-Reactive Derivative, Chapter 1, Section 1.6, http://www.lifetechnologies.com/us/en/home/references/molecular-probes-the-handbook/fluorophores-and-their-amine-reactive-derivatives/long-wavelength-rhodamines-texas-red-dyes-and-qsy-quenchers.html.*
Farouc A. Jaffer, et al., "In Vivo Imaging of Thrombin Activity in Experimental Thrombi with Thrombin-Sensitive Near-Infrared Molecular Probe," *Aterioscler Thromb. Vasc. Biol.*, 2002, 22:1929-1936.
Daisuke Kato, et al., "Activity-based probes that target diverse cysteine protease families," *Nat Chem Bio*, May 24, 2005, 1(1):33-38.
Doron C. Greenbaum, et al., "Small Molecule Affinity Fingerprinting: a Tool for Enzyme Family Subclassification, Target Identification, and Inhibitor Design," *Chem. Biol.*, 2002, 9:1085-1094.
Galia Blum, et al., "Dynamic imaging of protease activity with fluorescently quenched activity-based probes," *Nature Chemical Biology*, Aug. 14, 2005, 1(4):203-209.
Ralph Weissleder, et al., "In vivo imaging of tumors with protease-activated near-infrared fluorescent probes," *Nat. Biotechnology*, 1999, 17:375-378.
Johanna A. Joyce, et al., "Cathepsin cysteine proteases are effectors of invasive growth and angiogenesis during multistage tumorigenesis," *Cancer Cell*, 2004, 5, 443-53.
Ching-Hsuan Tung, et al., "In vivo Imaging of Proteolytic Enzyme Activity Using a Novel Molecular Reporter," *Cancer Res.*, 2000, 60:4953-4958.
Matthew Bogyo, et al., "Substrate binding and sequence preference of the proteasome revealed by active-site-directed site-directed affinity probes," *Chem Biol*, 1998, 5, 307-20.
Doron Greenbaum, et al., "Chemical approaches for functionally probing the proteome," *Mol Cell Proteomics*, 2002, 1, 60-8.

* cited by examiner

*Primary Examiner* — D L Jones
(74) *Attorney, Agent, or Firm* — David J. Aston; Peters Verny, LLP

(57) ABSTRACT

Methods and materials for the imaging of cells containing active proteases such as cathepsin are disclosed. The present materials include activity based probes that bind to an enzyme and are subsequently cleaved. Cleavage results in a fluorescent signal due to removal of a quenching group which, when present on the probe causes altered or no fluorescence. The probes employ an acyloxymethyl ketone reactive group, one or more amino acids for determining specificity, a fluorophore and a quencher. The probes are cell permeable and may use, for example, a QSY7 (diarylyrhodamine) quencher and a BODIPY (bora-diaza-indecene) dye.

3 Claims, 10 Drawing Sheets

A.
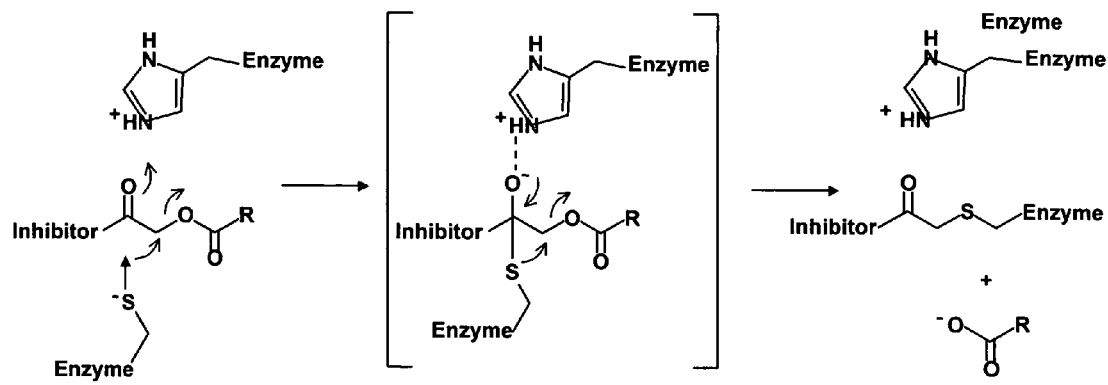
B.
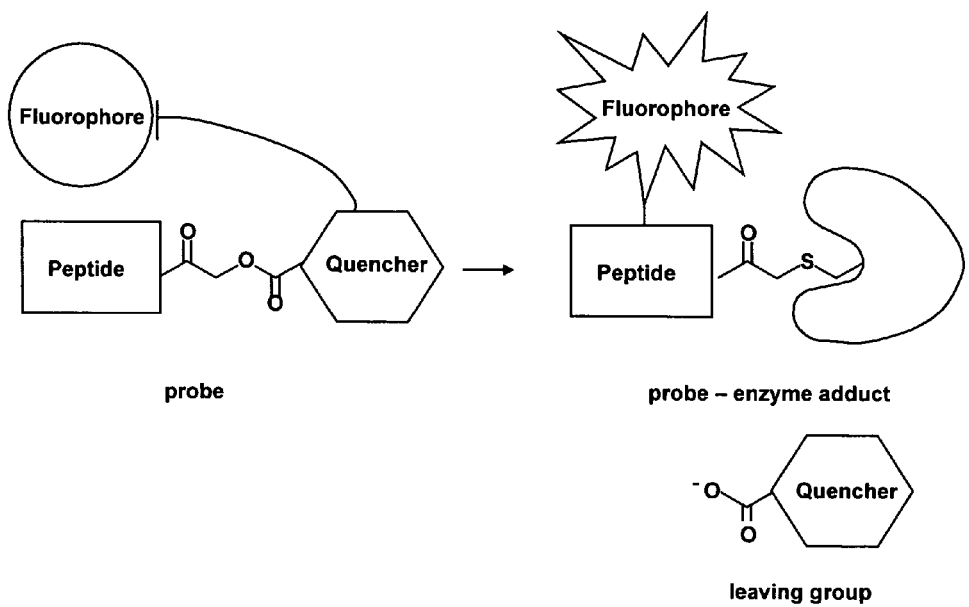
Fig. 1A-B

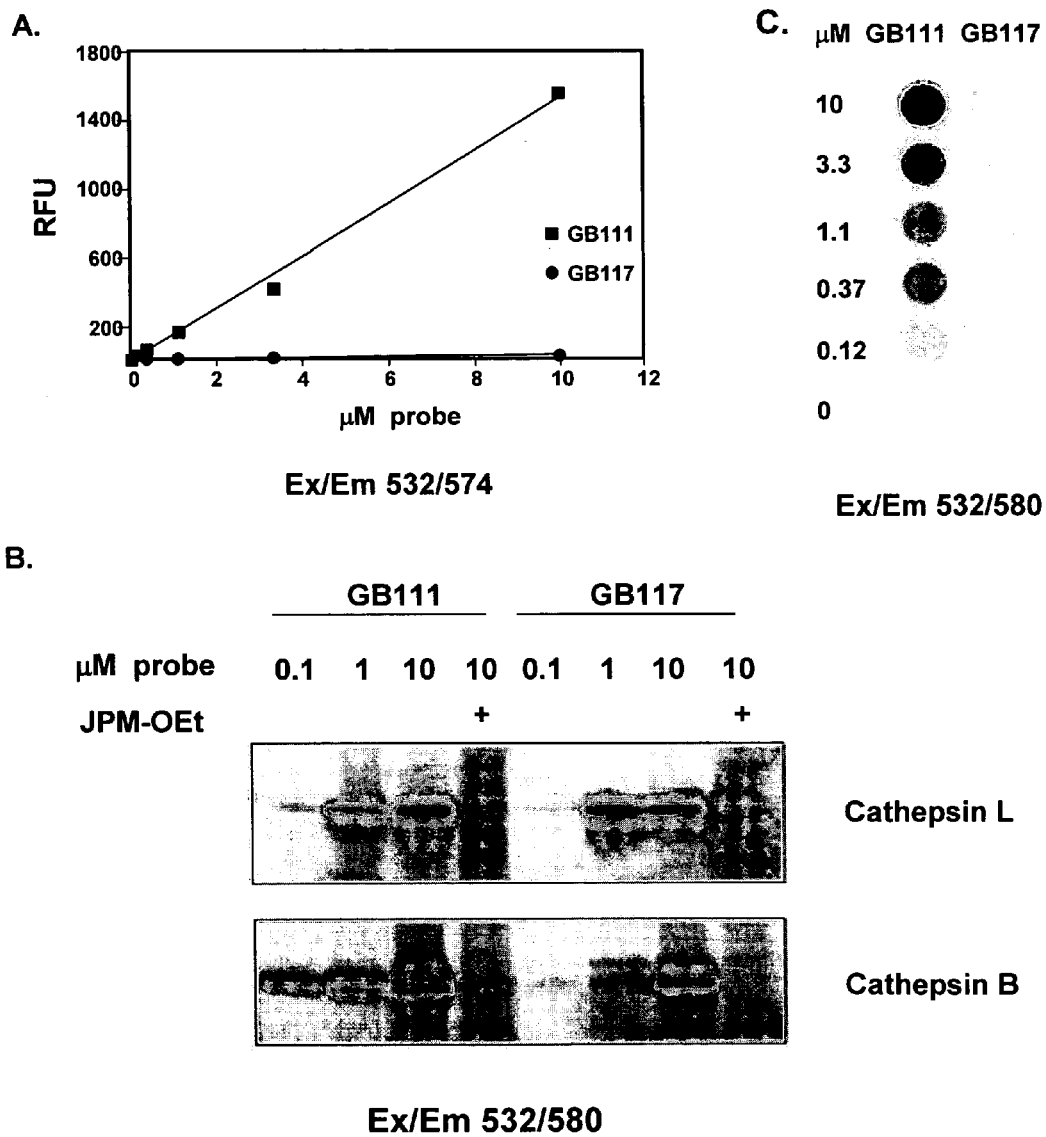
Fig. 2A-C

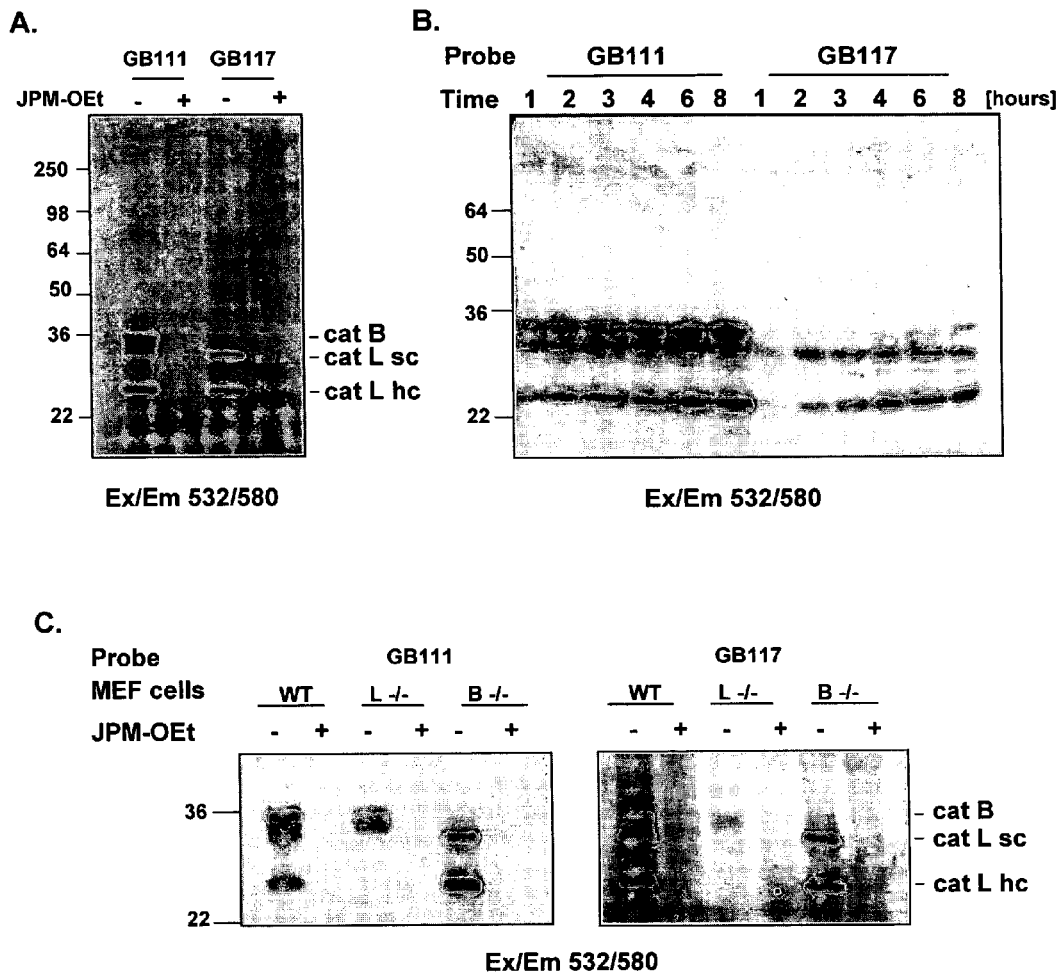
Fig. 3A-C

A.
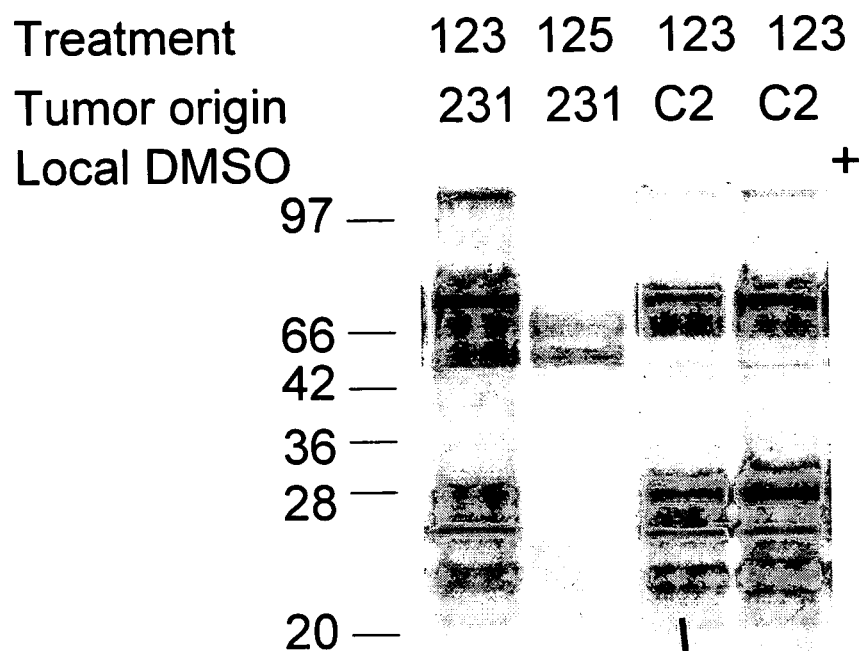
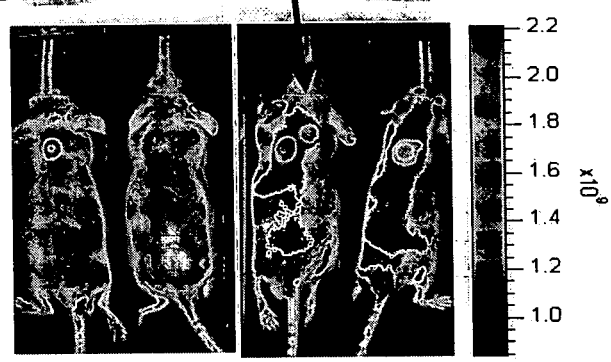
Fig. 6A

B.

QSY7 linker synthesis
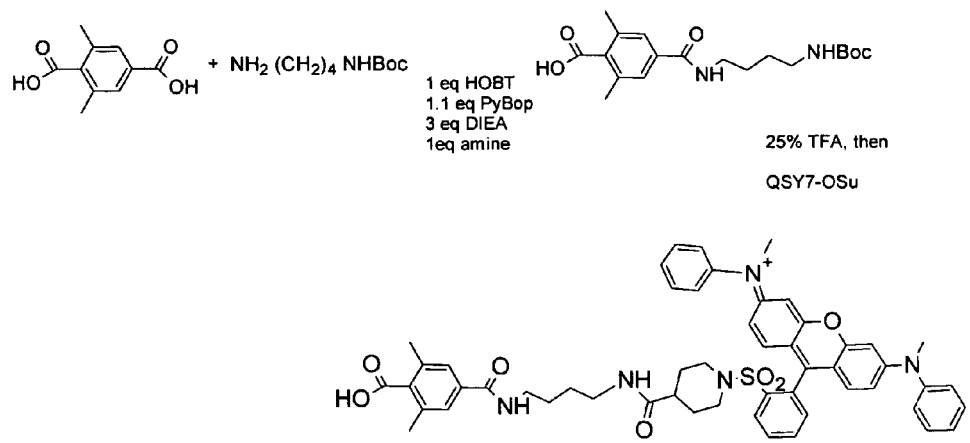
AOMK synthesis
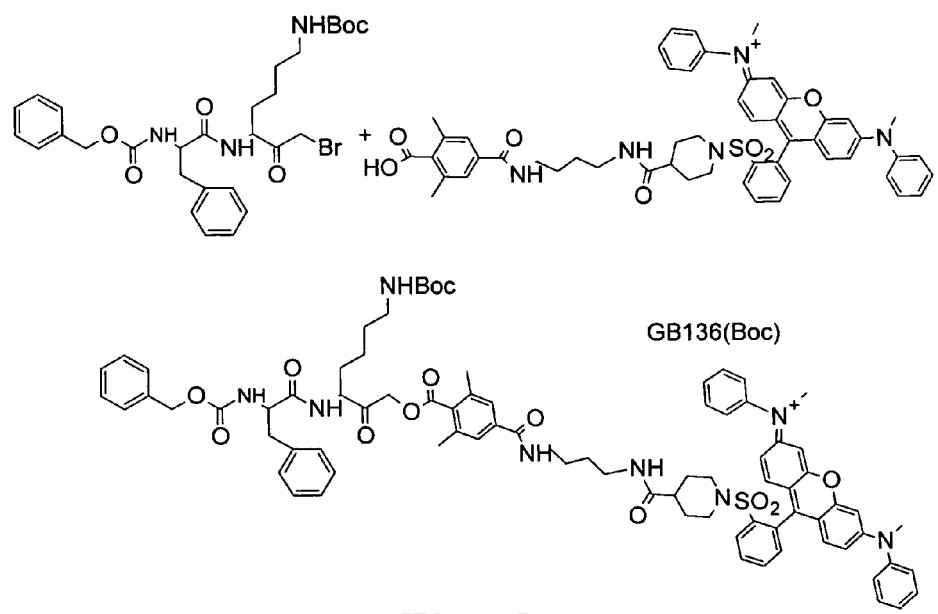
Fig. 8

IMAGING OF PROTEASE ACTIVITY IN LIVE CELLS USING ACTIVITY BASED PROBES

CROSS-REFERENCE TO RELATED APPLICATIONS

This application claims priority from U.S. Provisional Patent Application No. 60/707,249, filed on Aug. 11, 2005, which is hereby incorporated by reference in its entirety.

STATEMENT OF GOVERNMENTAL SUPPORT

This invention was made during work supported by National Technology Center for Networks and Pathways grant U54 RR020843. The government has certain rights in this invention.

REFERENCE TO SEQUENCE LISTING, COMPUTER PROGRAM, OR COMPACT DISK

None.

BACKGROUND OF THE INVENTION

1. Field of the Invention

The present invention relates to the field of imaging using organic molecules that bind specifically to active (but not inactive) proteases and also to compounds that change fluorescence upon binding.

2. Related Art

Background

Proteases play fundamental roles in the control of both normal and disease processes. Alterations in protease expression and activity patterns underlie many human pathological processes including cancer, arthritis, osteoporosis, atherosclerosis, and neurodegenerative disorders (Ref. 1). Thus, a detailed understanding of how, when and where a particular protease functions in a complex cellular environment is required to better understand its role in the promotion of disease. Perhaps the most powerful way to address these issues is to develop methods that allow dynamic imaging of protease activity within a living cell or organism. Protease activity is tightly regulated in both normal and disease conditions. Therefore, it is often difficult to monitor the dynamic nature of this regulation in the context of a live cell or whole organism.

Recently, a number of elegant methods have been developed to image enzymatic activities using both invasive and whole body imaging methods (for review see Ref. 2). Virtually all of these methods make use of reporter substrates that when processed by a given enzyme target produce a signal that can be visualized using common imaging modalities. While these methods have clearly paved the way for the application of activity based reporters to diagnostic medicine, they suffer from several features such as lack of specificity and cell permeability, as well as rapid diffusion that may limit their use in high-resolution studies of enzyme regulation and localization.

Activity based probes (ABPs) are small molecules that modify a defined set of enzyme targets based on their ability to form specific covalent bonds with key catalytic residues (for reviews see Refs. 3-7). Since this labeling reaction is mechanism-based and requires enzyme activity, extent of probe modification serves as an indirect readout of activity levels within a given sample. Probes can be designed to target a number of different classes of enzymes through optimization of both reactive functional groups and the scaffolds used to carry the reporter tag. In the past five years, a number of new classes of ABPs have been developed and used to dissect the function of various enzyme families (see reviews). The most well-established and heavily used probes are those that target proteolytic enzymes (Refs. 1-19). ABPs that target serine and cysteine proteases have been applied to studies of protease function in processes such as parasite invasion (Ref. 20), prohormone processing (Ref. 21), transcriptional regulation (Ref. 22), cataract formation (Ref. 23), natural killer cell function (Ref. 24), and cancer progression (Refs. 25-27).

A number of ABPs carrying a range of fluorescent reporters have also been described (Refs. 8, 12, 15, 27, 28). The fluorescent group serves as a highly sensitive tag that enables visualization of labeled targets after their biochemical separation. Fluorescently labeled ABPs have also been used to directly image enzyme activity using microscopy techniques. We recently demonstrated that a fluorescent ABP can be used in a mouse model for pancreatic cancer to image cysteine protease activity during multiple stages of tumor formation (Ref. 27). The use of ABPs for imaging applications has the major advantage of the formation of a permanent covalent bond with the enzyme, thus allowing direct biochemical analysis of targets. However, the major limitation of these probes is their general fluorescence both when bound to an enzyme target and when free in solution. To overcome this limitation there are disclosed here quenched probes (qABPs) that become fluorescent only after covalent modification of a protease target.

BRIEF SUMMARY OF THE INVENTION

The present invention is directed to activity based probes which bind to proteases. The probes of the invention comprise compounds with mono-, di-, tri- or tetra-peptide scaffolds. The peptide scaffold may be designed to bind specifically to the protease of interest, such as human cathepsin L. The peptide scaffold is linked to a fluorophore and an AOMK (acyloxymethyl ketone) group. The AOMK group is also linked to a quencher. Cleavage by the protease at the ester linkage of the AOMK group separates the fluorophore from the quencher, generating a signal associated with the bound enzyme. The compounds may be of a wide variety of structures, but may be represented generically by the formula

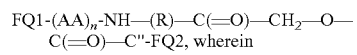

C(=O)—C"-FQ2, wherein

R extends from C as the side chain of any natural or non-natural amino acid;

C" comprises 0-10 carbon atoms in a linker to a quencher or fluorophore;

FQ1 and FQ2, taken together, are a fluorophore-quencher pair, and comprise optional linkers. FQ1 may be attached to any AA and may optionally be attached to a capping group of an aliphatic, aromatic, or heterocyclic ester, FQ2 is an optional quencher; AA is any amino acid, —C(=O)—CH2-O—C(=O)— represents an AOMK warhead, and n, representing the number of amino acid units, is 1-10.

In certain embodiments, the formula is FQ1-(AA)n-NH—(R)—C(=O)—CH2-O—C(=O)—C"-AR, in that no quencher is used, but an end group which facilitates synthesis, such as dimethyl benzoic acid, or other substituted aryl group is used.

For example, a lysine sidechain may be the R group bound to C'. A lysine-phenylalanine dipeptide is specifically within the scope of the present invention and is exemplified below.

A wide variety of FQ pairs may be used. As is understood in the art, a given compound may be either a fluorophore or a quencher, depending on the molecule that it is paired with for purposes of energy transfer. The FQ pair may be a bora-diaza-indecene, such as BODIPY, and a diaryl rhodamine, such as QSY7. Preferably, the quencher is in the portion of the molecule separated on cleavage.

In one aspect of the present invention, specific linkers have been found to be more stable in vivo and are incorporated to link a fluorophore or quencher to either an amino acid side chain, or the leaving end of the AOMK group, i.e., a group which binds to an enzyme and is thereby cleaved. Such linkers include alkyl groups such as isobutyric acid and aryl groups such as dimethyl benzyl groups.

The present compounds may be of the following representative formulas:

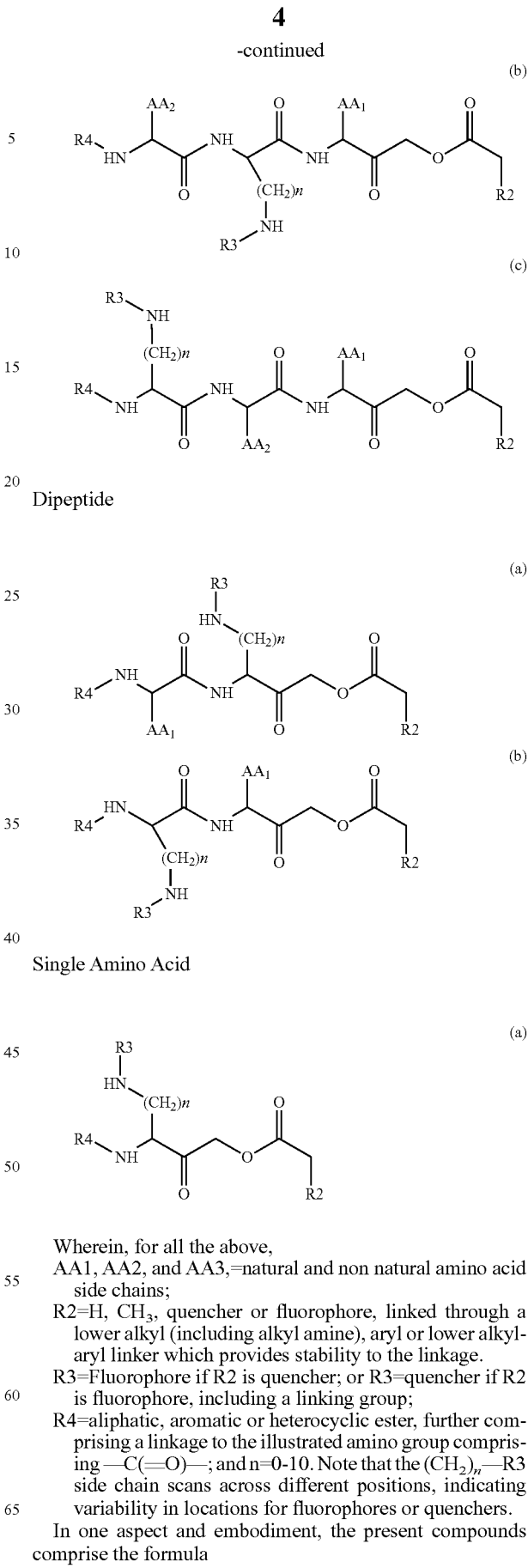

Tripeptide:

Dipeptide

Single Amino Acid

Wherein, for all the above,

AA1, AA2, and AA3,=natural and non natural amino acid side chains;

R2=H, CH$_3$, quencher or fluorophore, linked through a lower alkyl (including alkyl amine), aryl or lower alkyl-aryl linker which provides stability to the linkage.

R3=Fluorophore if R2 is quencher; or R3=quencher if R2 is fluorophore, including a linking group;

R4=aliphatic, aromatic or heterocyclic ester, further comprising a linkage to the illustrated amino group comprising —C(=O)—; and n=0-10. Note that the (CH$_2$)$_n$—R3 side chain scans across different positions, indicating variability in locations for fluorophores or quenchers.

In one aspect and embodiment, the present compounds comprise the formula

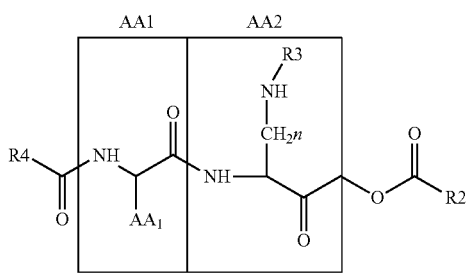

where the area in the adjacent rectangles represent 2-11 amino acid residues as set forth in the formulae above, wherein R3 may be present on any residue; for example, AA₁ may represent a phenylalanine side chain

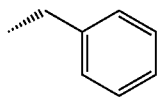

in the amino acid residue in the rectangle AA1,
R4 is a capping group, preferably methoxy benzyl:

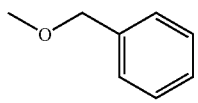

R3 is a fluorophore connected by a lower alkyl linkage, e.g., pentyl;
n is one to ten, preferably 4;
and R2 is a linker group, optionally bound to a quencher, i.e.

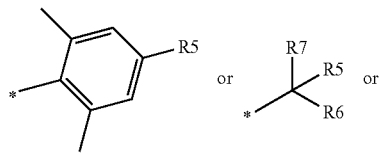

or
—(CH2)m-NH— Quencher or fluorophore
where R5=H, Linker to Quencher, or fluorophore;
R6 and R7=H, aromatic ester, aliphatic ester, or heterocyclic ester.

The term linker in the phase "Linker to Quencher" in connection with R5 refers to aliphatic groups as defined below which link the probe to a quencher.

The present invention also comprises methods of imaging using the quenched activity based probes. Such methods include a method of imaging a living organism, comprising:
(a) administering to said organism an acyloxymethyl ketone compound comprising an amino acid portion for binding to a predetermined protease, a fluorophore, and a quencher, said fluorophore and quencher separating upon binding and cleavage by the protease; and
(b) exposing said organism to electromagnetic radiation which excites non-quenched fluorophore to produce a detectable signal; and
(c) detecting said signal and creating an image thereby.

The methods may be applied to cellular, animal and medical studies. The probes may be administered by intravenous injection, direct injection to a specific site, and other means. Since protease activity is associated with tumor invasiveness and metastasis, the method has particular applicability to imaging a solid tumor, such as in breast cancer, which may be modeled by MCF-10A cells and other known model cell lines.

The fluorescence may be selected to be in the range of about 580-800 nm to take advantage of the relative transparency of tissue to IR light.

Also, the use of a spectral imager with the present methods has been found to provide improved resolution and sensitivity.

BRIEF DESCRIPTION OF THE DRAWINGS

FIG. 1 is a schematic diagram showing design of a qABP (quenched Activity Based Probe) FIG. 1a shows mechanism of covalent inhibition of a cysteine protease by an acyloxymethyl ketone. FIG. 1b shows activity dependent labeling of a cysteine protease target by a qABP. Covalent modification of the target results in loss of the quenching group resulting in production of a fluorescently labeled enzyme;

FIG. 2a is a graph showing determination of a quenching efficiency of the qABP GB117 in solution relative to the unquenched control ABP GB111. Solutions of the probes in buffer (pH5.5) at a range of dilutions were measured using a fluorescence plate reader (Molecular Devices) and plotted (left panel) or by direct scanning of solutions using a Typhoon (GE Healthcare) flatbed laser scanner (right panel, FIG. 2c). FIG. 2b is a pair of gels showing labeling of purified recombinant cathepsin B and L with the control ABP GB111 and the qABP GB117. Recombinant enzymes in buffer (pH 5.5) were either treated with the general papain family inhibitor JPM-OEt (50 μM of; +) or with DMSO (0.1%; −) for 30 minutes followed by labeling with probes at the indicated concentrations for 30 minutes. Samples were analyzed by SDS-PAGE and fluorescent signal measured by scanning of gels using a Typhoon laser flatbed scanner;

FIG. 3a is a gel showing intact monolayers of NIH-3T3 cells which were either pre-treated with the general papain family protease inhibitor JPM-OEt (50 μM) or with control DMSO (0.1%) for 1 hour and labeled by addition of GB111 and GB117 (10 μM) to culture media for 3 hours. After labeling cells were washed with PBS and harvested by direct lysis using SDS sample buffer. Crude detergent lysates were normalized for total protein, separated by SDS-PAGE, and visualized by scanning of the gel with a Typhoon flatbed laser scanner. FIG. 3b is a gel in which monolayers of NIH-3T3 cells were labeled by addition of GB111 or GB117 (10 μM) to cultured media for a series of times as indicated. Labeled proteases were analyzed as in a. FIG. 3c is a pair of gels showing labeling of cathepsin targets in fibroblasts derived from wild type (wt), cathepsin B deficient (cat B −/−) and cathepsin L deficient (cat L −/−) mice. Intact fibroblasts were pretreated with JPM-OEt (50 μM) or DMSO (0.1%) for 1 hour followed by labeling with either the control ABP GB111 (left) or the qABP GB117 (right). Cells were collected, lysed and analyzed after SDS-PAGE as in a and b;

FIG. 6 is a photograph of a gel (FIG. 6a) and corresponding photographs of mice treated with inhibitors GB 123 and GB 125 and implantation of different tumor cell lines, MDA-MB-231 and C2/C12/ras.

FIG. 8 is a reaction scheme showing synthesis of a QSY® 7 linker and an AOMK warhead with capping group and a quencher.

DETAILED DESCRIPTION OF THE PREFERRED EMBODIMENT

Introduction

Figure 4:
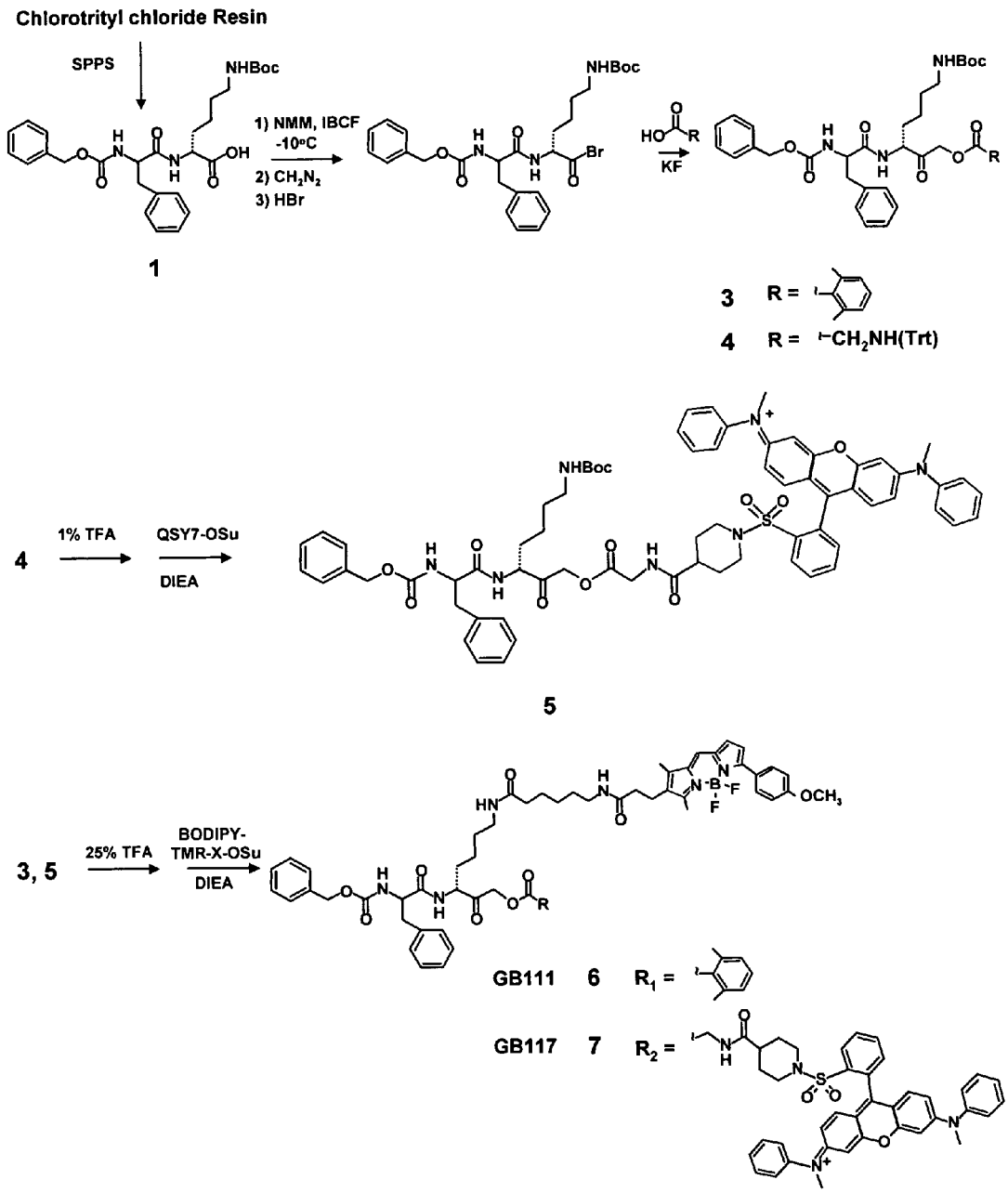
FIG. 4 is a schematic diagram showing synthesis of the qABP GB117 and the corresponding control ABP GB111. The fully protected di-peptide (1) was synthesized on solid support using standard solid phase peptide synthesis (SPPS) and was converted to the corresponding BMK (2) in solution. The resulting BMK was converted to the 2,6-dimethyl benzoic acid AOMK (3) or the N-trityl-protected glycine AOMK (4). Selective removal of the N-trityl group from (4) followed by coupling of the QSY 7 quencher yielded AOMK intermediate (5). Finally, removal of the Boc-protecting group on lysine of (3) and (5) followed by coupling of the BODIPY-TMR-X yielded the final products GB111 and GB117.

Described below is a series of quenched—and unquenched—activity based probes (qABPs) that become fluorescent upon activity-dependant covalent modification of a protease target. These reagents freely penetrate cells and allow direct imaging of protease activity in living cells. Targeted proteases are directly identified and monitored biochemically by virtue of the resulting covalent tag thereby allowing unambiguous assignment of protease activities observed in imaging studies. Further described is the design and synthesis of a selective, cell permeable qABP for the study of papain family cysteine proteases. This probe is used to monitor real-time protease activity in living cells using fluorescence microscopy techniques as well as standard biochemical methods. Proteases to be monitored in Family CA (the papain family) include cathepsins B and L (cancer involvement), cathepsin K (bone degradation) and parasitic enzymes essential for the parasite-host interaction (e.g., cruzipain from *Trypanosoma cruzi*—causing Chagas' disease, and falcipain from *Plasmodium falciparum* causing malaria.

Definitions and Abbreviations

Abbreviations: NMM—N-methyl morpholine, IBCF—Isobutylchloroformate, HBr—hydrogen bromide, TFA—trifluoroacetic acid, DIEA—Diisopropylethylamine, qABP—quenched activity based probe, AOMK—acyloxymethyl ketone.

The terms "activity based probe" and "warhead" are used here according to their accepted meanings, namely compound which is an enzyme inhibitor which acts by binding to a specific enzyme and inactivating through chemical modification (typically covalent binding) to the active site of the enzyme. The portion of the activity-based probe (ABP) that chemically binds to the enzyme is termed the "warhead." The warhead is attached to a pseudosubstrate, i.e., a compound similar to one or more, preferably 2-3, amino acids in the substrate of the enzyme to be inhibited. The enzyme acts on proteins and is typically a protease with a specific recognition sequence. Thus the term warhead includes AOMK, epoxy, nitrile and other known reactive groups. The remainder of the molecule contains 1-3 amino acid or amino acid-like residues. Further clarification of these terms may be found in U.S. Pat. No. 6,777,403 to Cheronis, issued Aug. 17, 2004, entitled "Method and structure for inhibiting activity of serine elastases."

The term "fluorophore" means a fluorescent molecule, i.e., one that emits electromagnetic radiation, especially of visible light, when stimulated by the absorption of incident radiation. The term includes fluorescein one of the most popular fluorochromes ever designed, which has enjoyed extensive application in immunofluorescence labeling. This xanthene dye has an absorption maximum at 495 nanometers. A related fluorophore is Oregon Green, a fluorinated derivative of fluorescein. The term further includes bora-diaza-indecene, rhodamines, and cyanine dyes. The term further includes the 5-EDANS (Nucleotide analogs adenosine 5'-triphosphate [g]-1-Naphthalenesulfonic acid-5(2-Aminoethylamide) (ATP[g]-1,5-EDANS) and 8-Azidoadenosine 5'-triphosphate [g]-1-Naphthalenesulfonic acid-5(2-Aminoethylamide) (8N3ATP[g]-1,5-EDANS).

The term "bora-diaza-indecene" means compounds represented by 4,4-difluoro-4-bora-3a,4a-diaza-s-indacene, known as BODIPY® dyes. Various derivatives of these dyes are known and included in the present definition, e.g., Chen et al. "4,4-Difluoro-4-bora-3a,4a-diaza-s-indacene (BODIPY) dyes modified for extended conjugation and restricted bond rotations," J Org Chem. 2000 May 19; 65 (10):2900-6. These compounds are further defined in reference to the structures set out below under the heading "FLUOROPHORES." In the exemplified BODIPY TMR-X, R1 in fluorophores=benzyl methoxy; the structure is further shown in Scheme 1. The linker is an amide bond to the lysine side chain chosen as part of the dipeptide starting material.

The term "rhodamine" means a class of dyes based on the rhodamine ring structure. Rhodamines include (among others): Tetramethylrhodamine (TMR): a very common fluorophore for preparing protein conjugates, especially antibody and avidin conjugates; and carboxy tetramethyl-rhodamine (TAMRA) used for oligonucleotide labeling and automated nucleic acid sequencing. Rhodamines are established as natural supplements to fluorescein based fluorophores, which offer longer wavelength emission maxima and thus open opportunities for multicolor labeling or staining. The term is further meant to include "sulfonated rhodamine," series of fluorophores known as Alexa Fluor dyes.

The dramatic advances in modern fluorophore technology are exemplified by the Alexa Fluor dyes introduced by Molecular Probes (Alexa Fluor is a registered trademark of Molecular Probes). These sulfonated rhodamine derivatives exhibit higher quantum yields for more intense fluorescence emission than spectrally similar probes, and have several additional improved features, including enhanced photostability, absorption spectra matched to common laser lines, pH insensitivity, and a high degree of water solubility. Also related to rhodamine dyes is TAMRA.

The term "cyanine" means a family of cyanine dyes, Cy2, Cy3, Cy5, Cy7, and their derivatives, based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethyl-rhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations.

Marketed by a number of distributors, the cyanine dyes are readily available as reactive dyes or fluorophores coupled to a wide variety of secondary antibodies, dextrin, streptavidin, and egg-white avidin. The cyanine dyes generally have broader absorption spectral regions than members of the Alexa Fluor family, making them somewhat more versatile in the choice of laser excitation sources for confocal microscopy.

The term "quencher" means a compound that modulates the emission of a fluorophore. A quencher may itself be a fluorescent molecule which emits fluorescence at a characteristic wavelength. Thus a fluorophore may act as a quencher when appropriately coupled to another dye and vice versa. In this case, increase in fluorescence from the acceptor molecule, which is of a different wavelength to that of the donor label, will also indicate binding of the ABP. Alternatively, the acceptor does not fluoresce (dark acceptor). Such acceptors include DABCYL, methyl red, QSY-7® diarylrhodamine dyes and 6-(dimethylamino)-2-[4-[4 (dimethylamino)phenyl]-1,3-butadienyl]-1-ethyl quinolinium perchlorate (CAS number 181885-68-7). Typical fluorophore/quencher compounds include certain rhodamine dyes or Cy5.

The term "aryldiazo" refers to quenching compounds such as 4 (4'dimethylaminophenylazo)benzoic acid (DABCYL), a common dark quencher used widely in many assays, such as "molecular beacons" for DNA detection (U.S. Pat. No. 5,989, 823).

Diazo dyes of the BHQ series, which are referred to as "Black Hole Quenchers" (International Patent Publication No. WO 01/86001), provide a broad range of absorption, which overlaps, well with the emission of many fluorophores. The QSY series dyes from Molecular Probes are another series of dark quenchers used extensively as quenching reagents in many bioassays (U.S. Pat. No. 6,399,392).

The structure of QSY 7® is illustrated in Sriram Kumaraswamy et al., US Patent Publication 2005/0014160, "Assays for protease enzyme activity." QSY-7 is a nonfluorescent diarylrhodamine derivative.

Fluorophore/quencher pairs are illustrated for use in DNA labeling in Lee, "Detection System," United States Patent Application 20040241679, published Dec. 2, 2004.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to ten carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred. The term lower alkyl includes substituted alkyl, such as "perfluoro-lower alkyl", which refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred. Also included are "alkoxy", which the group R'—O—, wherein R' is alkyl. The term "lower-alkoxy" refers to the group R"—O—, wherein R" is lower-alkyl. Examples of lower alkoxy groups are e.g., methoxy, ethoxy, propoxy, isopropoxy, butoxy, isobutoxy and hexyloxy, with methoxy being especially preferred. Also included is "lower alkylthio", which refers to the group R'—S—, wherein R' is lower-alkyl as defined above.

The term "aryl" refers to an aromatic monovalent mono- or polycarbocyclic radical, such as phenyl and naphthyl, preferably phenyl. Substituted aryl is aryl that is mono-, di- or tri-substituted, independently, by lower alkyl, lower alkoxy, halogen, amino or perfluoro-lower alkyl, preferably by lower alkyl, lower alkoxy and halogen.

Accordingly, "aryl-lower alkyl" means an aryl group linked to a lower alkyl group. An example of aryl-lower alkyl is found in GB 136, where a quencher is linked to an AOMK warhead by a linker comprising p,p dimethyl benzoic acid amide linked to an n-butyl group.

The present compounds may be made through the use of solid phase peptide synthesis techniques, which will employ known protective groups, capping groups, and the like. The term "capping group" refers to group has the effect of preventing further chemical reactions from occurring at that site, and is a non-amino acid moiety bonded to the C- or N-terminal of the peptide chain. Examples of common N-terminal capping groups used in peptide synthesis are Boc (t-butoxycarbonyl,) and Cbz (benzyloxycarbonyl). Other capping groups useful in synthesis are acetyl and adamantyl, dimethyl benzyl succinimidyl, 4-methylbenzyl, 2-thiophenylmethyl, 4-thiazolylmethyl, 3,5-difluorobenzyl, etc. A preferred capping group for use as $FQ_2$ is dimethyl benzoic acid.

EXAMPLE 1

Design and Synthesis of Reactive Probes

Unless otherwise noted, all resins and reagents were purchased from commercial suppliers and used without further purifications. All solvents used were of HPLC grade. All water-sensitive reactions were preformed in anhydrous solvents and under positive pressure of argon. Reactions were analyzed by LC/MS using an API 150EX (Applied Biosystems). Reverse-phase HPLC was conducted with an ÄKTA explorer 100 (Amersham Pharmacia Biotech) using C18 columns. High-resolution MS analyses were performed by Stanford Proteomics and Integrative Research Facility using a Bruker Autoflex MALDI TOF/TOF mass spectrometer. Fluorescent scanning of gel and plates were done using a Typhoon 9400 (GE Healthcare) flatbed laser scanner (Amersham Biosciences).

The exemplified embodiments below focus on the acyloxymethyl ketone (AOMK) reactive group for probe design as this "warhead" targets diverse families of cysteine proteases (Refs. 9, 29). More importantly, the mechanism of covalent modification of a cysteine protease by an AOMK involves the loss of its acyloxy group (Ref. 29) (FIG. 1a). Thus, a probe carrying a fluorescent reporter group on its peptide scaffold and a highly efficient quenching molecule attached to the acyloxy leaving group should result in a quenched probe that only becomes fluorescent upon covalent labeling of an enzyme target (FIG. 1b). We initially focused our efforts on probes that target the papain family of cysteine proteases as this family has been extensively studied using ABPs and a number of cell permeable reagents have successfully been designed (Refs. 9, 11, 14, 15). Our first generation of qABPs made use of the fluorescein/4-([4-(Dimethylamino)phenyl]azo) benzoic acid (DABCYL) pair which was shown to be effective for related applications (Refs. 30, 31). Unfortunately, we found that while it was possible to use cell permeable BODIPY analogs of fluorescein, the DABCYL group prevented probes from freely entering cells (data not shown). Furthermore, we found that direct attachment of the DABCYL quenching group to the reactive hydroxy ketone methylene resulted in probes that were highly unstable in aqueous solution and in addition showed dramatically reduced potency for target proteases, presumably due to the proximity of the bulky quencher to the active site (data not shown). We therefore shifted our attention to the larger but potentially more cell permeable quenching group QSY-7 and attached this group to the probe through a linker to improve stability and potency.

The synthesis of the resulting quenched probe GB117 and its corresponding non-quenched control GB111 was carried out using a combination of solid and solution phase chemistries (Scheme 1). This synthetic route was chosen over recently reported solid-phase methods (Ref. 9) due to the formation of an intra-molecular acyl transfer reaction on resin that was observed when an aliphatic acyloxy group was used in place of the 2,6-dimethyl benzoic acid group. The fully protected carboxyl benzoyl capped phenylalanine-lysine di-peptide (1) was synthesized using standard solid phase peptide synthesis and was converted to the corresponding bromo-methyl ketone (2; BMK) in solution. Coupling of 2,6-dimethyl benzoic acid with the BMK resulted in the AOMK intermediate (3) for use in the synthesis of the non-quenched control. Conversion of the BMK (2) using N-trityl protected glycine yielded the AOMK (4) that was coupled to the commercially available QSY7 quenching group after removal of the trityl group to produce intermediate (5). Finally, removal of the Boc protecting group on the sidechain of lysine in intermediates (3) and (5) allowed attachment of the BODIPY-TMR-X fluorophore to produce the desired ABP GB111 (compound 6) and qABP GB117.

Solid phase peptide synthesis of peptide was carried out as follows: (Compound 1 in FIG. 4): 2-Chlorotrityl chloride resin was loaded by shaking of resin with Fmoc Lysine(Boc) OH (1.5 eq), and Diisopropylethylamine (DIPEA) (3 eq) dissolved in anhydrous $CH_2Cl_2$ for 1 hour. Methanol (1 ml/gr resin) was added, the resin was shaken for 20 min. and subsequently was washed with $CH_2Cl_2$ and DMF. Fmoc was removed by incubation with 20% piperidine/DMF (v/v) for 20 min followed by $CH_2Cl_2$ and DMF washes. The peptides were elongated by addition of a solution of N-benzyloxycar-bonyl-phenylalanine (3 eq), DIPEA (3 eq) and diisopropyl-carbodiimide (DIC) (3 eq) in DMF for 2 hours. The resin was washed with $CH_2Cl_2$ and DMF and the final fully-protected peptide product was cleaved from resin by addition of 1% TFA/DCM (v/v) for 15 min. The cleavage solution was collected and solvent was removed by coevaporation with toluene. The crude peptide was further dried in vacuo to yield a white solid that was deemed greater than 85% pure by LC/MS and was used without further purification (1, 99% yield relative to resin loading).

Synthesis of bromomethyl ketone (2): To a solution of 1 (0.47 mmol) in anhydrous THF at −100 C, were added sequentially N-methylmorpholine (0.59 mmol, 1.25 eq) and isobutyl chloroformate (0.53 mmol, 1.15 eq). The solution was stirred for 25 minutes at −100 C followed by addition of excess ethereal diazomethane (~5 eq) that was generated in situ as described. The solution was warmed to room temperature over 3 hours while stirring. A solution of 22% hydrogen bromide, 44% acetic acid and 34% water (1.5 mL) was added dropwise and the resulting solution stirred for an additional 3 min at 0° C. The reaction was stopped by addition of ethyl acetate followed by washing of the organic phase with water, brine solution and saturated $NaHCO_3$. The final organic layer was dried over $MgSO_4$ and solvent was removed in vacuo to obtain a white solid that migrated as a single peak by LC/MS analysis and was used for subsequent steps without further purification (0.55 mmol, 91% yield).

Synthesis of acyloxymethyl ketones (3) and (4): The crude peptide BMK (2) (0.25 mmol), potassium fluoride (2.5 mmol 10 eq) and 2,6-dimethylbenzoic acid (1.25 mmol, 5 eq) were dissolved in anhydrous DMF under argon and stirred overnight. The DMF solvent was removed by rotary evaporation. DCM was added to the crude residue and the resulting organic phase was washed with water, brine and saturated NaHCO3. The organic phase was dried over $MgSO_4$ and solvent was removed in vacuo to obtain (3) as a white solid that was used without further purification (0.22 mmol, 88% yield). The AOMK (4) was obtained using a similar procedure except N-trityl glycine was used instead of 2,6-dimethylbenzoic acid. Crude (4) was purified by C18 reverse phase HPLC using water-acetonitrile gradient without TFA, product was eluted with 90% acetonitrile, to obtain (4) as a white solid (0.065 mmol, 25% yield).

Synthesis of peptide acyloxymethyl ketone (5): The N-trityl of AOMK (4) (0.01 mmol) was removed in the presence of the Lys(Boc) by addition of 1% TFA in $CH_2Cl_2$ (1 ml) for 45 min. The solvent was removed by co-evaporation with toluene to yield the crude free amine product. A solution of 0.05 mg/μl QSY 7 (6.32 μmol, 0.6 eq) in DMSO was added to the crude amine of (4) followed by DIPEA (19 μmol 3 eq). The reaction was stirred in the dark for 8 hours. During this time 5 more eq of DIPEA were added. The resulting product (5) was directly purified from the crude reaction mixture by C18 reverse phase HPLC using water-acetonitrile gradient. The product was eluted with 70% acetonitrile, to obtain a purple solid (2.08 μmol), 33% yield.

Synthesis of GB111 (compound 6) and GB117 (compound 7): The N-e-Boc was removed from intermediates 3 (47 μmol) or 5 (1.15 μmol) by addition of a solution of 25% TFA in $CH_2Cl_2$ for 1 hour. The solvent was removed by co-evaporation with toluene, the crude free amine products were used without further purification. A solution of 0.05 mg/μl BODIPY TMR-X succinimidyl ester (0.9 eq, 4.1 μmol) in DMSO, the crude free amine of (3) (4.52 μmol) and DIPEA (2 eq, 8.2 μmol) was agitated and allowed to stand in the dark for 3 hours. Crude (6, GB111) was obtained by direct purification from the crude reaction mix by C18 reverse phase HPLC using water-acetonitrile gradient, product was eluted with 75% acetonitrile, to obtain pink solid, (2.4 μmol), 58% yield. Compound (7, GB117) was obtained similarly using 1.03 μmol BODIPY TMR-X succinimidyl ester, 1.15 μmol (5) free amine and 2 μmol DIPEA. The product was purified by HPLC and the product was eluted with 75% acetonitrile, to obtain dark purple solid, (0.74 μmol, 72% yield). High-resolution mass spectrometer (HRMS) data: [MNa]+ calculated for GB111, C60H69BF2N6NaO9, 1089.5085; found 1089.5537; (HRMS) [MH]+ calculated for GB117 C92H99BF2N10O13S+, 1632.7169; found 1632.7099.

Evaluation of In vitro Quenching of the qABP

Dilutions of the GB111 or GB117 in acetate buffer (50 mM acetate, 5 mM $MgCl_2$, 2 mM DTT, pH 5.5) containing final 1% DMSO in a 96 well plate were measured using a fluorescence plate reader (Molecular Devices) excitation/emission 535/574 nm. Relative Fluorescent units (RFUs) were plotted verses probe concentration. The plate was then directly scanned using a Typhoon (GE Healthcare) flatbed laser scanner excitation/emission 532/580 nm.

Recombinant Cathepsin Labeling of the qABP.

0.7 μg recombinant human Cathepsin L (a generous gift from Dr. V. Turk Jozef, Stefan institute Slovenia) or 0.4 μg bovine Cathepsin B (Sigma) in reaction buffer (50 mM acetate, 2 mM DTT and 5 mM MgCl2, pH 5.5) were treated with 25 μM JPM-OEt for 30 min (indicated samples) at room temperature. Increasing concentrations of GB111, GB117, were added to appropriate samples for 30 min. The reaction was stopped by adding sample buffer X4 (40% glycerol, 0.2M Tris/HCl 6.8, 20% β-mercaptoethanol, 12% SDS and 0.4 mg/ml bromophenol blue). Half of the sample was separated on a 12% SDS gel and scanned by a Typhoon laser flatbed scanner at 532/580.

The synthetic scheme and exemplary compounds can be readily adapted to create a series of probes, according to the general formulas below. They are based on scaffolds having either 1, 2, 3 or 4 amino acids, one of which is labeled, attached to an AOMK group through an ester bond. On the other side of the ester bond is a quencher. When the probe binds, the quencher is released as the ester bond is hydrolyzed. The present ABPs are illustrated above as tetrapeptide probes, tripeptide probes, dipeptide probes, or single amino acid probes. As can be seen from the exemplary structures, the present compounds comprise a peptid-like backbone, an AOMK warhead, and a linker and quencher attached to either the AOMK warhead or the peptide backbone through a linker. A number of different peptide-like sequences are known to give substrate specificity, and may be adapted for use with the present fluorophore/linker combinations.

The above formulas shown in the Brief Summary of the Invention are further exemplified by compounds described below, GB 119, GB 123, GB 125 and GB 135. These compounds have structures illustrated as follows:

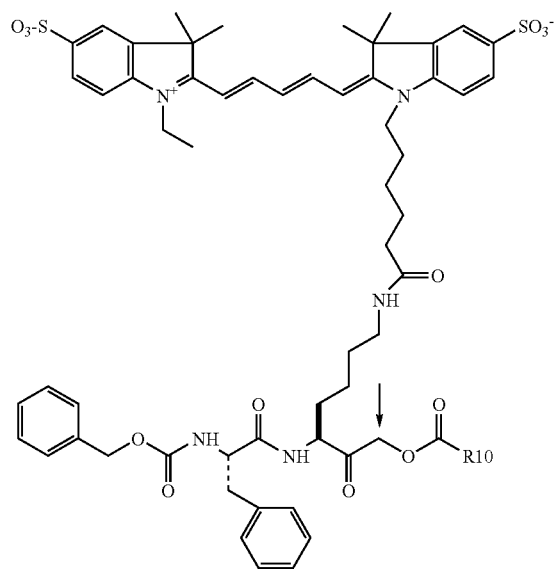

In GB 119, R10 is a quencher having a direct linkage connecting at the *:

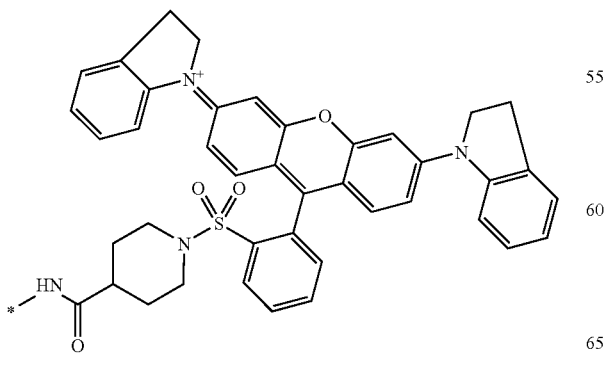

In GB 123, R10 is a dimethylbenzyl (i.e., no quencher):

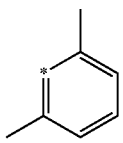

In GB 125, R10 is replaced by an amino group at the arrow in the above generic structure, i.e., a control with no active AOMK group.

In GB 135, R10 is a quencher having an alkyl spacer, derived from isobutyric acid:

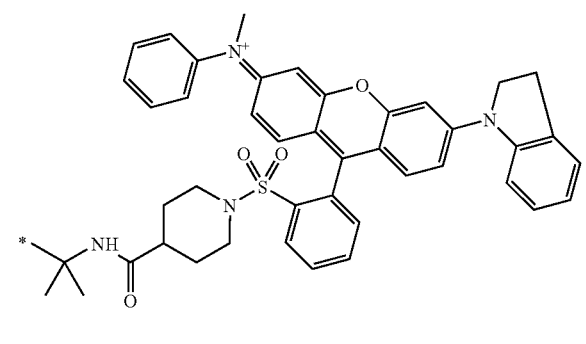 [SMILES: C/[N+](c1ccccc1)=c1/ccc2c(-c3ccccc3S(=O)(=O)N3CCC(C(=O)NC(C)(C)C)CC3)c3ccc(N4CCc5ccccc54)cc3oc-2c1]

In the above exemplary compounds the fluorophore (e.g., as attached to the lysine side chain in GB 123) is Cy 5 for fluorescence in the near IR region. The quencher (used in R10) is QSY 21.

A similar compound is GB 136, wherein the linker is dimethyl benzoate-NH—(CH$_2$)$_4$—:

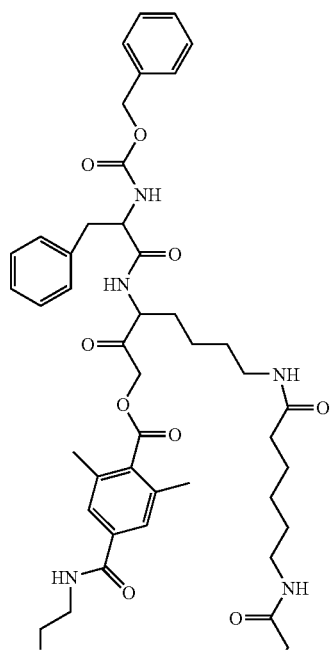

-continued

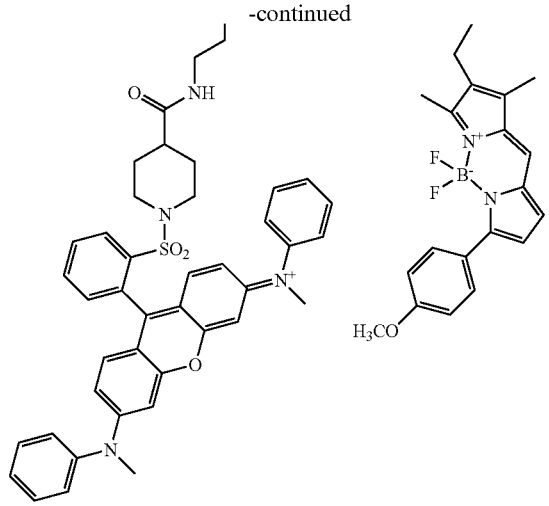

Exemplary Fluorophores

BODIPY® Analogs
(4,4-difluoro-4bora-3A,4A-diaz-S-indacene)
Analogs

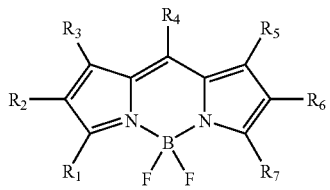

R1=H, CH3, C6H5, C4H3X (X=S, NH), C6H4OCH3, (CH=CH)C6H5, (CH=CH)2C6H5, CH2CH2COOH, CH2CH2CO—
R2=H, Br
R3=H, CH3, C6H5
R4=H, CH2CH2CO—
R5=H, CH3
R6=H, Br, CH2CH2CONH(CH2)5CO—
R7=H, CH3, (CH2)2CO—,(CH2)2COOH, C6H4OCH2CONH(CH2)5CO—, (CH2)4CO—, CH2CH2CONH(CH2)5CO—, CH2CH2CONHCH(CH2SO3-)CO—

Fluorescein Derivatives

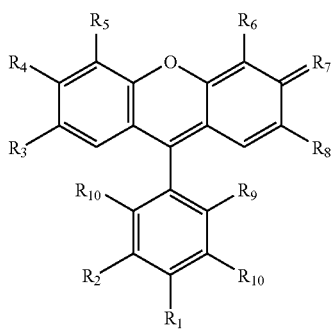

-continued

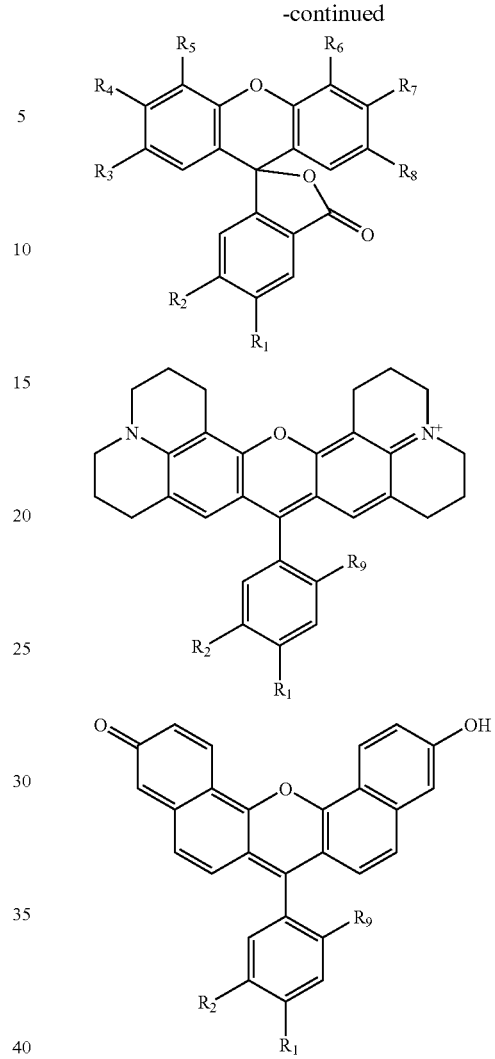

R1, R2=H, CO—, COOH,

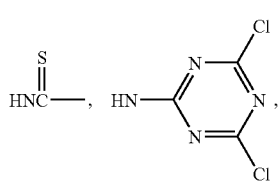

CONH(CH2)5CO—,
NHCOCH2SCH2CH2CO—, F, N(CH3)2, N(CH3CH2)2, SO2NH(CH2)5CO—, SO3-
R3, R8=F, Br, Cl, I, CH3, OCH3
R4=O, NHCOCF3, NH2, NHCH2CH3
R5, R6=Br, Cl, SO3-
R7=O, OCOCF3, NHCOCF3, NH2, NHCH2CH3
R9=COOH, SO3-, SO3H, SO2NH(CH2)5CO
R10=Cl

17
Dansyl (5-dimethylaminonaphthalene)
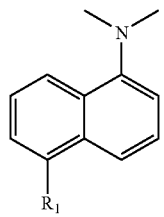
R1=CO—, SO2-, SO2NH—
Alexa Fluors
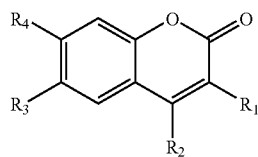
Alexa Fluor 350
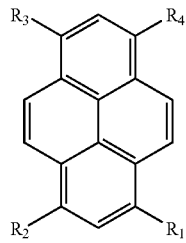
Alexa Fluor 405
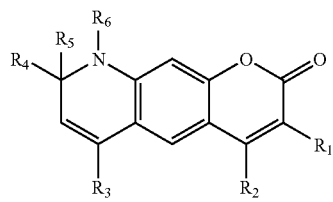
Alexa Fluor 430
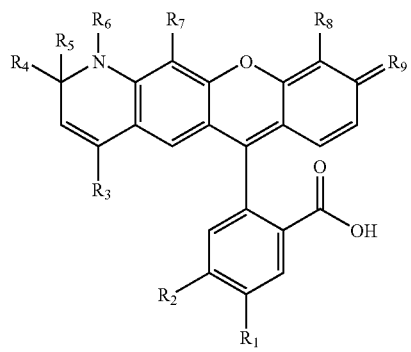
Alexa Fluor 514
18
-continued
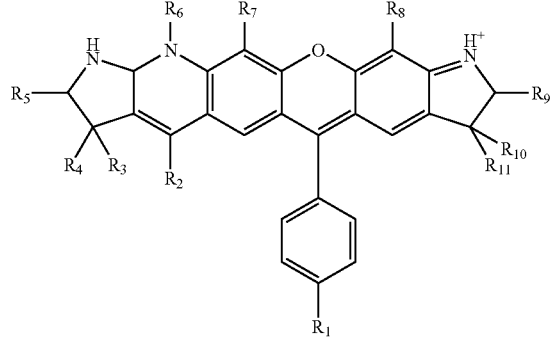
Alexa Fluor 532
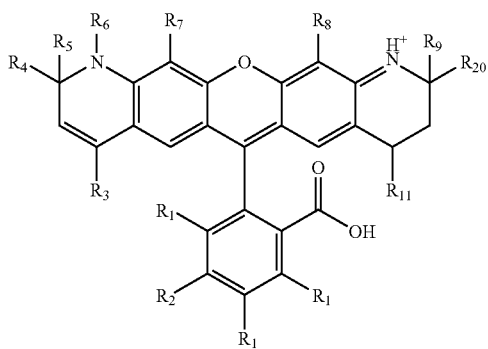
Alexa Fluor 546, 568, 594, 610
R=H, CH3, SO3-, CF3 CH2SO3-, CH2SO3H, (CH2)5, SO3, Cl, SCH2CONH(CH$_2$)$_5$CO—, CO—
Cy Fluorophores
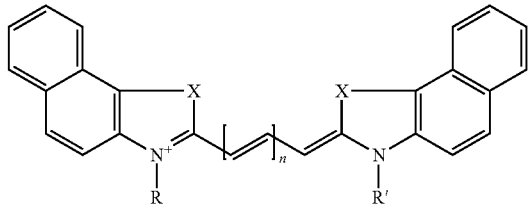
X=O, NR, C(CH3)2, S, Se
R, R'=alkyl aryl
n=0-5
Exemplary Quenchers
QSY Quenchers
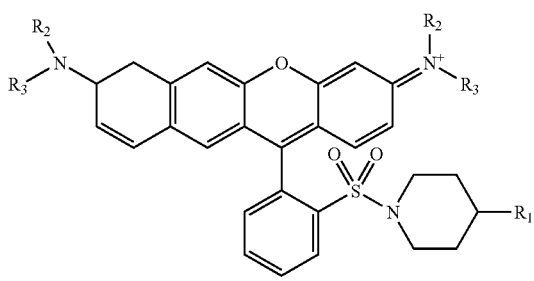

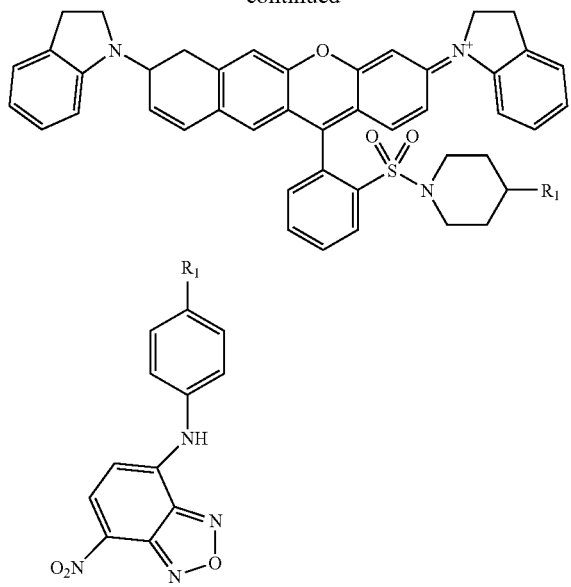

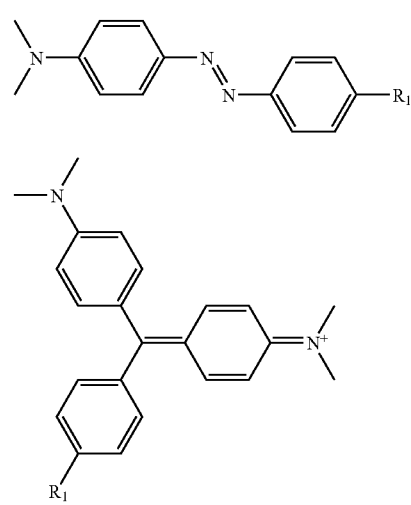

R1=CO—, SO2-, SO2NH—,

R1=CO—, CONH—, CONH(CH2)5NH—, (CH2)5CO—, CONH(CH2)5CO—, CH2NHCO—

R2, R3=CH3, C$_6$H$_5$, C$_6$H$_4$SO3+

QSY 21 quencher, as obtained from Invitrogen, QSY® 21 carboxylic acid, succinimidyl ester, has the following structure:

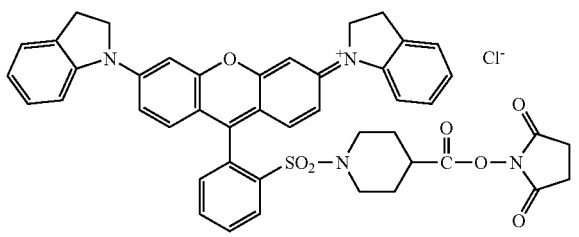

The succinimidyl ester facilitates the linkage of the quencher to a linking group on the compound to be labeled, as can be seen in connection with GB 135. Thus, the terminal amide in the linkers used herein is considered part of the quencher. QSY quenchers are analogs of fluorescein.

With regard to the amino acids used in the present compounds, any naturally occurring amino acid may be used. In addition, the amino acids of the peptides of the present invention may also be modified. For example, amino groups may be acylated, alkylated or arylated. Benzyl groups may be halogenated, nitrosylated, alkylated, sulfonated or acylated. The following is an exemplary list of chemically modified amino acids may be incorporated into the present compounds:

Acetylated

N-acetyl-L-alanine, N-acetyl-L-arginine; N-acetyl-L-asparagine; N-acetyl-L-aspartic acid;
N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine;
N-acetyl-L-threonine; N-acetyl-L-tryptophan; N-acetyl-L-tyrosine; N-acetyl-L-valine.

Amidated

L-alanine amide
L-arginine amide

Formylated

N-formyl-L-methionine

Hydroxylated 4-hydroxy-L-proline

Lipid Modified

S-farnesyl-L-cysteine
S-geranylgeranyl-L-cysteine

Others

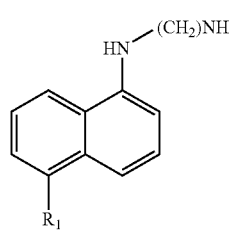

EDANS

N-palmitoyl-L-cysteine
S-palmitoyl-L-cysteine
N-myristoyl-glycine
N6-myristoyl-L-lysine Methylated N-methyl-L-alanine
N,N,N-trimethyl-L-alanine
omega-N,omega-N-dimethyl-L-arginine
L-beta-methylthioaspartic acid
N5-methyl-L-glutamine
L-glutamic acid 5-methyl ester
3'-methyl-L-histidine
N6-methyl-L-lysine
N6,N6-dimethyl-L-lysine
N6,N6,N6-trimethyl-L-lysine
N-methyl-L-methionine
N-methyl-L-phenylalanine Phosphorylated omega-N-phospho-L-arginine
L-aspartic 4-phosphoric anhydride
S-phospho-L-cysteine
1'-phospho-L-histidine
3'-phospho-L-histidine
O-phospho-L-serine
O-phospho-L-threonine
O4'-phospho-L-tyrosine Other L-selenocysteine
L-selenomethionine
L-3-oxoalanine
2-pyrrolidone-5-carboxylic acid
L-glutamyl 5-glycerylphosphorylethanolamine
2'-[3-carboxamido-3-(trimethylammonio)propyl]-L-histidine (diphthamide)
N6-biotinyl-L-lysine
N6-(4-amino-2-hydroxybutyl)-L-lysine (hypusine)
N6-retinal-L-lysine The naturally occurring amino acid side chains are illustrated below, in which * represents the attachment point to the compound's backbone:

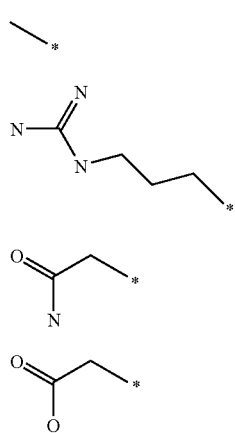

Choice of Fluorophore and Quencher Pairs for Imaging

As described, a wide variety of fluorophores and quenchers are available for use with the present ABPs. The fluorophore and the quencher must be appropriately paired so that a detectible signal is generated when the probe binds to the protease and is cleaved. One may employ principles learned from FRET imaging to choose appropriate molecular pairs that will yield clear signals.

FRET, or fluorescence resonance energy transfer, is the non-radiative transfer of photon energy from a donor fluorophore to an acceptor fluorophore when both are located within close proximity (1-10 nm). Using FRET one can prepare a qABP with a donor and acceptor on portions of the molecule that physically separate when the probe binds to the protease target. Before cleavage, when the donor fluorophore is excited by light it transfers its excited state energy to a light absorbing molecule (the acceptor). This transfer of energy is non-radiative, due primarily to a dipole-dipole interaction between donor and acceptor. Thus in choosing appropriate pairs, one would consider the following prerequisites:
1. The donor's fluorescence emission spectrum overlaps (to some extent) the excitation spectrum of the acceptor
2. The donor fluorescence has a sufficiently long lifetime (ns)
3. The donor and acceptor dipole orientations must be approx. parallel
4. The distance between donor and acceptor is small (about 1-10 nm)

A great many fluorophores have been examined for FRET. A review of FRET principles is found in Selvin, "The renaissance of fluorescence resonance energy transfer," *Nature Structural Biology* 7(9), 730-734 (2000).

An excellent overview of FRET including the conditions for FRET and the FRET equation is available online from the Molecular Probes Handbook of Fluorescent Probes and Research Products at http://probes.invitrogen.com/handbook.

Primary Conditions for FRET (from the Molecular Probes Handbook) include the following: Donor and acceptor molecules must be in close proximity (typically 10-100 Å, which is 1-10 nm. For comparison the diameter of a DNA double helix is 2.3 nm, an F-actin filament ~6 nm, an intermediate filament ~10 nm, and a microtubule 25 nm).

Absorption spectrum of the acceptor must overlap fluorescence emission spectrum of the donor. Donor and acceptor transition dipole orientations must be approximately parallel (for optimal energy transfer).

In standard FRET imaging one excites the donor fluorophore with excitation light, and collects sequentially the fluorescence emission of the donor and acceptor. For the donor-acceptor pair of fluorescein-rhodamine one might use a 470-490 nm excitation filter, and a 500-520 nm emission filter for collecting the light from the fluorescein donor. One might then use a 600-650 nm emission filter for collecting the light from the rhodamine acceptor. These emission filters need to collect just the shorter wavelength range of the donor, and just the long emission tail of the acceptor, to avoid cross-talk between the two image channels. That is, one would want to avoid collecting fluorescein emission in the rhodamine channel and vice versa. The problem is that for FRET to work, the donor emission and acceptor excitation spectra must overlap (high overlap is good), but for good signal-to-noise ratio imaging one must avoid collecting the "wrong" photons through a filter.

A potential alternative collection method is to use a spectral imaging device that would collect all the photons of both the donor and acceptor simultaneously and somehow separate out the two on the basis of their spectra. One would still excite fluorescein from 470-490 nm, but one would collect all the emission photons from 500-650 nm simultaneously. A device that should be able to do this is a fluorescence microscope with the suggested 470-490 nm/500-650 nm filter cube and an Applied Spectral Imaging, Inc., SpectraCube® spectral imaging device. The SpectraCube® is a Fourier transform interferometer spectral imaging device that attaches to a standard microscope (i.e., Axioplan-2, Axioskop-2, Eclipse E800, or their inverted microscope equivalents) by a C-mount adapter. The device collects all the photons all the time, and uses clever mathematical analyses to quantify the amount of each fluorophore by their spectra. Using an interferometer allows the device to "collect all the photons all the time" and compute the spectrum later (offline).

EXAMPLE 2

Testing of Potency and Quenching/Labeling by Probes

We attached the fluorophore to the probe at the P1 lysine side-chain in order to optimize proximity to the quenching group. Previous work has shown that the majority of critical substrate interactions take place in the P2 position of the papain family proteases (Ref 32). This close positioning resulted in a probe that showed greater than 70-fold quenching when compared to the non-quenched control probe (FIG. 2a). This amount of quenching is sufficient for imaging applications and is in line with other reported proximity-induced quenching reagents (Ref 30). When we performed kinetic inhibition studies for the two papain family proteases cathepsins B and L we found that modification of the P1 lysine of the free amine intermediate of GB111 (NH2-GB111) resulted in a 100-fold loss of potency towards cathepsin L and 30 fold loss of potency for cathepsin B (Table 1). Determination of kinetic rate constants of inhibition.

The kinetics of inhibition was determined by progress curve method under pseudo-first order conditions with at least 10-fold molar excess of inhibitor. Recorded progress curves were analyzed by non-linear regression according to the following equation (Ref 36).

$[P] = v_z(1-e^{-k \cdot t})/k$ where $[P]$ is the product, vz is the velocity at time zero and k is the pseudo first order rate constant. Apparent rate constant (kapp) was determined from the slope of plot k versus [I]. Due to irreversible and competitive mechanism of inhibition, kapp was converted to the association constant (kass) using the equation below:

$$k_{ass} = k_{app}(1+[S]/K_M)$$

Activity of human cathepsin L was measured using the fluorogenic substrate Z-FRAMC37 (Bachem, USA) (Km=7.1 μM) and cathepsin B was assayed against the fluorogenic substrate Z-RR-AMC38 (Bachem, USA) (Km=114 μM). Concentration of substrates during the measurement was 10 μM. Cathepsins B and L (1 nM final concentrations) were incubated with inhibitor concentrations, ranging from 10 to 2000 nM, in the presence of 10 μM of appropriate substrate. Total volume during the measurement was 100 μl. Increase of fluorescence (370 nm excitation, 460 mm emission) was continuously monitored for 30 minutes by Spectramax M5 spectrofluorimeter.

(Molecular Devices, USA) and inhibition curves were recorded. DMSO concentration during all measurements was 3.5%.

TABLE 1

Inhibition rate constants of various probes for human cathepsin L and bovine cathepsin B.

| | $k_{ass}[M^{-1}s^{-1}]$ | | | |
|---|---|---|---|---|
| | GB111 | GB117 | GB111-NH$_2$ | GB111-B oc |
| Cathepsin L | 2580 ± 800 | 7000 ± 1200 | 296400 ± 18100 | 1180 ± 120 |
| Cathepsin B | 1256 ± 308 | 275 ± 66 | 38500 ± 7700 | 212 ± 15 |

The resulting fluorescent probes retained significant activity that was deemed sufficient to obtain efficient labeling of targets. Interestingly, replacement of the 2,6-dimethyl benzoic acid group on GB111 with the bulky QSY7 quencher resulted in a larger drop in potency of the probe towards cathepsin B than towards cathepsin L (Table 1). This result can most likely be explained by the so-called occluding loop of cathepsin B blocking access of extended peptides into the prime side binding sites 33. Modeling of the two probes into the high-resolution structures of cathepsins B and L confirmed that the QSY7 group potentially produces van der Waals clashes with the occluding loop of cathepsin B.

We next examined if GB111 and GB117 were capable of forming stable covalent linkages to cathepsin targets. Labeling of purified recombinant cathepsin B and L confirmed the kinetic results and demonstrated that both probes label the recombinant enzyme in solution resulting in an SDS-stable covalent linkage (FIG. 2b). This labeling could also be specifically competed by pre-treatment of the enzymes with the broad-spectrum papain family cysteine protease inhibitor JPM-Oet (Ref. 27). Furthermore, the same drop in potency of GB117 towards cathepsin B was observed in the in vitro labeling profiles thus confirming the relative selectivity of GB117 for cathepsin L.

EXAMPLE 3

Use of Probes in Cultured Cells

Having confirmed that both the qABP and the control probe label multiple papain family proteases in vitro at reasonable kinetic rates we set out to determine if these probes could label endogenous enzyme targets in intact cells. The probes were added to monolayers of live NIH-3T3 cells followed by collection, lysis of cells and analysis by SDS-PAGE (FIG. 3a). These initial results confirmed that both probes freely penetrated cells and labeled a series of protease targets in a highly selective way. Furthermore, the probes show virtually no background labeling when papain family proteases were inactivated by pre-treatment of cells with JPM-OEt. Kinetic analysis of the labeling of the protease targets indicated that GB117 had a slower rate of modification than did GB111 suggesting that extended labeling times would be required to obtain optimal signal (FIG. 3b). Interestingly, the pattern of proteases labeled by GB111 included a species around 33 kDa that was only faintly labeled by GB117 at extended time points. We predicted that this species might be cathepsin B based on its size and our findings that suggested that GB117 has reduced potency towards this target (Table 1 and 1 g. 2b). To confirm the identity of the labeled species we performed similar experiments in intact fibroblast cells derived from wild type and cathepsin B and L knock-out mice (FIG. 3c). As expected the 33 kDa species labeled efficiently by GB111 and only very poorly by GB117 was absent in the cathepsin B deficient cells. Furthermore, the two remaining species that were labeled by both probes were absent in the cathepsin L knock-out cells. These two bands represent the full-length single chain form and cleaved heavy chain form of cathepsin L and are the two predominant active forms of cathepsin L observed in previous labeling studies[22]. Thus, the qABP and control probe freely penetrate cells and show highly specific labeling of cathepsin B and L in multiple cell lines.

Based on the positive biochemical results in the NIH-3T3 cells, we began fluorescent imaging studies in these cells using both probes. Treatment of live monolayers of cells with GB 111 followed by immediate imaging of the live cells using confocal fluorescence microscopy showed intense, non-specific staining of the entire cell, presumably as a result of free probe accumulation. The Invitrogen amine-reactive dye, BODIPY TMR-X, SE, has fluorescence characteristics similar to tetramethylrhodamine (excitation/emission is 544/570 μm) and can be used to fluorescently tag peptides. The non-specific nature of this signal was confirmed by the persistence of the signal after pre-treatment with the general inhibitor JPM-OEt. In contrast, when cells were incubated with GB117 and imaged without washing, a distinct punctate labeling pattern was observed. This pattern was found to overlap with signal from the acidotropic lysosomal marker Lysotracker and could be blocked by pre-treatment of cells with the general inhibitor JPM-OEt. This pattern was highly consistent with specific labeling patterns that we had observed previously with fluorescent epoxide probes after extensive washing of the cells[15,27]. To confirm our analysis of the imaging data we treated cells with GB111 and then performed extensive washing prior to microscopy based imaging.

In these experiments (data not shown), cultures of NIH-3T3 cells were either pre-treated with the general papain family protease inhibitor JPM-OEt (50 μM) or with control DMSO (0.1%) for 1 hour and labeled by addition of GB111 or GB117 (1 μM) to growth media for 4-5 hours. The acidotropic lysosomal marker LysoTracker (which produces a green color) was added and cells were imaged using an inverted fluorescent microscope (Nikon). Cells were also treated and analyzed after being washed for 3 hours in growth media containing JPM-OEt (50 μM) or DMSO (0.1%) prior to imaging. As a result, red fluorescence—indicating protease activity, green fluorescence—indicating lysosomal compartments, and yellow fluorescence resulting from overlap in green and red signals was observed. The unquenched GB111 showed a general staingin roughly comparable to the area of staingin of the lysotracker. The quenched GB 117 showed puctate staingin that was inhibited by JPM-OEt, the general protease inhibitor.

As expected, the resulting images closely matched those observed for GB117. These results confirm that GB117 is fluorescently activated upon binding to protease targets and this method provides sufficient signal over noise to allow direct real-time analysis of protease activity in live cells that have not been fixed or washed.

Cell Cultures

NIH-3T3 mouse fibroblast cells were a generous gift from Dr. Peter Jackson (Stanford University, CA). Cells were cultured in DMEM supplemented with 10% FBS, 100 units/mL penicillin, 100 μg/mL streptomycin. Mouse embryo fibroblasts (MEF) wild type (WT) and MEF cells derived from the cathepsin L knockout (Roth et al., 2000) (Cat L−/−) were a generous gift from Dr. Alain Nepveu (McGill University, Canada). MEF cells derived from the cathepsin B knockout were isolated and characterized in the Sloane laboratory (Demchik and Sloane, personal communication). Cells were cultured in DMEM supplemented with 10% FBS, 100 units/mL penicillin, 100 μg/mL streptomycin. MCF-10A cells were a kind gift from Dr. Joan Brugge (Harvard, Cambridge, Mass.); MCF-10A cells were cultured in DMEM/F12 supplemented with 5% donor horse serum, 20 ng/mL EGF, 10 μg/mL bovine insulin, 0.5 μg/mL hydrocortisone, and 1× antibiotic-antimycotic. All cells were cultured in a humidified atmosphere of 95% air and 5% CO2 at 37° C.

Labeling of Intact Cells with the Control ABP and qABP.

NIH 3T3 cells (250,000 cell/well) were seeded in a 6 well plate 1 day prior to treatment. Cells were pre-treated with the general papain family protease inhibitor JPM-OEt (50 μM) or with control DMSO (0.1%) for 1 hour and labeled by addition of GB111 and GB117 in DMSO at a given concentration to culture media at pH 7.4 for indicated hours.

The final DMSO concentration was kept at 0.2%. Cells were washed with PBS and lysed by addition of sample buffer (10% glycerol, 50 mM Tris/HCl, pH 6.8, 3% SDS, and 5% β mercaptoethanol). Lysates were boiled for 10 min and cleared by centrifugation. Equal amounts of protein per lane were separated by 12% SDS-PAGE, labeled proteases were visualized by scanning of the gel with a Typhoon flatbed laser scanner (Ex/Em 532/580 nm). Mouse embryonic fibroblasts (MEF) WT, Cat L–/– and Cat B–/– cells were labeled similarly as described above with few changes, MEF WT and Cat L–/– were seeded at 240,000 cell/well, MEF Cat B–/– were seeded 300,000 cells/well. 1 µM GB111 or GB117 was incubated with cells for 4.5 hours.

Imaging Protease Activity in Live Cells.

NIH 3T3 cells (165,000 cells/well) were seeded on glass cover slips in six-well tissue culture plates containing growth medium 1 day before treatment. Cells were either pretreated with the general papain family protease inhibitor JPM-OEt (50 µM) or with control DMSO (0.1%) for 1 hour. Cells were labeled by addition of GB111 or GB117 (1 µM) to growth media at pH 7.4 for 4-5 hours. Cells were transferred to growth media without phenol red. LysoTracker (50 nM final concentration) was added minutes before cells were imaged using an inverted fluorescent microscope (Nikon Diaphot-300 microscope with the 60 (NA 1.4) objective). Cells were washed with growth media with JPM-OEt (50 µM) or with control DMSO (0.1%) for 3 hours and imaged.

EXAMPLE 4

Use of Probes in Three Dimensional Cell Culture

This was done to apply the qABP to studies of more complex cell culture models. We chose to focus on a 3D cell model that more accurately mimics human cancers (Ref. 34). The fibrocystic breast cell line MCF-10A forms highly organized three-dimensional spheroids when grown on reconstituted basement membranes (Cultrex). These structures recapitulate several aspects of glandular architecture in vivo and are therefore considered to be an excellent cellular model for various forms of tumor growth (Ref. 35). Since these cells presumably import and secrete components of the matrix we reasoned that we should be able to apply the probes by direct addition to the matrix prior to seeding of cells. After 3 days of growth on matrix containing the probes acinar structures had formed. Imaging of the samples grown on matrix containing the unquenched probe GB111, produced bright, non-specific intracellular fluorescent staining similar to what was observed in the monolayers (data not shown).

In these experiments, reconstituted basement membrane, Cultrex (Trevigen) was mixed with 1 µM GB111 or GB117 with or without JPM-OEt (50 µM). MCF-10A cells were grown three-dimensional cultures on Cultrex containing probes with or without inhibitor for 3 days then imaged by confocal microscopy using a water immersion lens (Zeiss).

Interestingly, the free probe in the matrix did not show any significant fluorescence suggesting a quenching effect by matrix proteins. Cells incubated on matrix containing the quenched probe GB117 showed distinct punctate staining of lysosomal compartments (data not shown). Furthermore this staining could be completely blocked by addition of the general inhibitor JPM-OEt, suggesting that it represents specific staining of active proteases. To confirm that the staining in the GB111 treated spheroids was due to background from free probe, we treated day 8 spheroids with GB111 and then washed and fixed the cells. Imaging of these spheroids showed specific staining similar to that observed in the live cells treated with GB117.

The resulting pattern of probe labeling partially overlapped with immunofluorescent staining of the same fixed cells using an anti-cathepsin B antibody. Interestingly, it appears that the population of active cathepsin B labeled by the probe is found predominantly at the apical pole of the cells in the acini although the total distribution of staining for is both apical and basal.

MCF-10A cells were grown in 3D culture on reconstituted basement membrane extracted from an EHS mouse sarcoma (Cultrex from Trevigen) as previously described 35. GB117 or GB111 was added to Cultrex (1 µM final concentration) upon cell seeding and day 3 structures were imaged as described below. Day 8 structures grown Cultrex without probes were treated with 1 µM GB111 for 3 hours in assay media (culture media with 2% horse serum and 5 ng/mL EGF). Cells were washed overnight in assay media, fixed and imaged as described below.

Immunofluorescence analysis: Cells in 3D culture were fixed on day 8 with cold methanol for 10 minutes and washed with PBS 3 times at 10 minutes per wash. Structures were then blocked for 1 hour in IF buffer (130 mM NaCl, 7 mM Na2HPO4, 3.5 mM NaH2PO4, 7.7 mM NaN3, 0.1% bovine serum albumin, 0.2% triton X-100, 0.05% TWEEN 20) and incubated with a rabbit anti human cathepsin B (produced and characterized in the Sloane lab39) or rabbit anti-human procathepsin L (a gift from M. Gottesman, NCI) antibodies overnight at 4° C. Structures were washed three times with PBS for 20 minutes per wash, then incubated with corresponding secondary antibodies for 2 hours at room temperature, followed by three washes with PBS for 20 minutes each. Structures were incubated with 1 µg/mL DAPI in PBS for 10 minutes, then washed three times with PBS. Samples were imaged using a 40× water immersion lens on a Zeiss LSM 510 confocal microscope.

EXAMPLE 5

In Vivo Whole Animal Imaging

Photographs illustrating fluorescence imaging of endogenous cathepsin activity in live mice using the quenched activity-based probe GB117 were obtained with the CR1-Maestro™ Spectral imager, and comparisons were made between mice (a) with no probe, (b) with GB117 and (c) with GB117 plus the general cathepsin inhibitor JPM-OEt. Raw emission spectrum (580-720 nm) showed mainly autofluorescence that was similar in all 3 mice, independently of whether GB117 was injected. No specific fluorescence was seen in the control mouse.

The calculated, unmixed signal specific for GB117 probe showed signal only in the case of GB117 without JPM. That is, injection of GB117 (10 micromole/kg of body weight) via the tail vein followed by imaging 4 hours later lead to substantial labeling of the entire mouse reflecting endogenous cathepsin activity in superficial tissues such as skin and blood. Areas of more intense labeling in the center of the animal (likely labeling of the liver, an organ with high cathepsin activity) were seen. On the other hand, pre-treatment of the mouse with the general cysteine cathepsin inhibitor JPM-OEt (100 mg/kg IP injection) 2 hours prior to injection of GB117 significantly reduced fluorescent signal in the entire animal suggesting that the signal observed results from labeling of active proteases.

This work utilized a spectral imager (CRI Maestro) at the small animal imaging facility at Stanford. This new technology makes it possible to acquire the entire spectrum of light emission. Following spectral acquisition, the wavelengths specific to the injected probe can be defined, and autofluorescence subtracted. This procedure results in a substantially increased signal to noise ratio. Techniques for spectral imaging in connection with multiple chromosome labels ("chromosome painting") are known and may be adapted for use in vivo. See U.S. Pat. Nos. 5,936,731 and 6,690,817. A spectral imager is capable of collecting spatial (imaging) information as well as spectral information at every pixel in the image. This 3 dimensional data set enables the detailed study of both absorptive and fluorescent, histological and cellular material. It may be used to detect and separate the spectral "finger prints" of different markers (proteases or probes), which may also be in differing environments, and to map their spatial arrangement and colocalization These experiments indicate that following injection of the quenched probe GB117 via the tail vein, the entire mouse shows increased labeling, reflecting endogenous cathepsin activity. Notably, the area of the liver appears to show increased cathepsin activity, as expected. In contrast, if the mouse was pretreated with the general cathepsin inhibitor JPM, no specific fluorescence was seen after injection of the probe. Interestingly, the tail shows substantial specific fluorescence in both mice injected with the quenched probe, independently of whether the mouse was pretreated with the cathepsin inhibitor JPM. This most likely reflects a small amount of highly-concentrated probe (1 mM) that has leaked out of the vessel and infiltrated the surrounding tissue during tail vein injection and that, although quenched, shows some fluorescence due to the high concentration.

EXAMPLE 6

In Vivo Imaging of Cysteine Protease Activity Using the Cy5-Labeled Probe GB123

Three weeks prior to imaging, MDA-MB 435 or MDA-MB 231 cells ($3 \times 10^6$ cell per site) were subcutaneously injected into the back left and right side of a Balb-c nude mouse. As is known in the literature, MDA-MB-435, expresses ALP56 (aspartic-like protease 56 kDa), which has homology to aspartic proteases, such as cathepsin D. Similarly, a trypsin-like protease secreted from MDA MB-231 cells can promote cell migration through autocrine activation of PAR-2.

Figure 5:
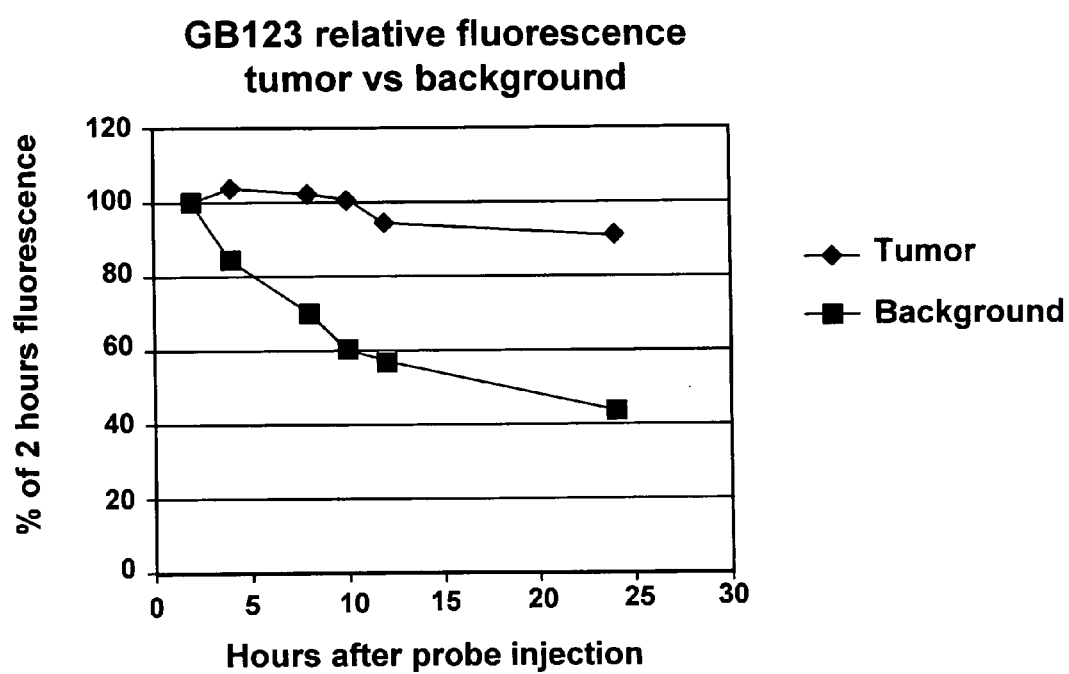
FIG. 5 is a graph showing GB123 relative fluorescence in tumor vs. background.

GB123 (1 µg) dissolved in DMSO/PBS was injected via the tail vein. Fluorescent images of living mice taken using an IVIS 200 imaging system equipped with a Cy5.5 filter at various time points after GB123 injection show localization of the probe to a tumor site. The accumulation of fluorescent signal was observed over time in MDA-MB 231 tumors and to a lesser extent in the MDA-MB 435 tumors. Labeling of active cysteine proteases in cell lines used to generate the tumors was carried out on SDS-PAGE. Intact monolayers of MDA MB-231 or MDA MB-435 cells were either pre-treated with the general papain family protease inhibitor JPM-OEt (50 µM) or with control DMSO (0.1%) for one hour and labeled by addition of GB123 (1 µM) to culture media for four hours. Crude detergent lysates were normalized for total protein, separated by SDS-PAGE, and visualized by scanning of the gel with a Typhoon flatbed laser scanner. The increased labeling of a number of cysteine protease activities in MDA-MB 231 relative to the MDA-MB 435 cells was seen. All of these specific activities were sensitive to pre-treatment with the general inhibitor JPM-OEt. FIG. 5 shows results obtained when relative fluorescence was measured in MDA-MB 231 tumor from the in vivo study and compared to an averaged background signal from back and leg regions of interest (ROIs). Plotted values are expressed as percentage of fluorescence measured relative to the signal observed at two hours post injection of probe.

EXAMPLE 7

In vivo Labeling of Live Mice with Active Probe GB123 (no Quencher) and Control Inactive Probe GB125 in Mice with Multiple Tumor Types Two to four weeks prior to imaging MDA-MB 231 or C2C12/ras cells (a myoblast cell line wherein ras blocks differentiation) at $2 \times 10^6$ cell per spot were injected subcutaneous to the back of Balb-c nude mice.

Mice bearing tumors of similar size were injected intravenous via the tail vein with a DMSO/PBS solution of GB123 or GB125 (0.8-1.1 µg/gr mice). DMSO/PBS was locally injected directly into tumors in indicated mice, 15 minutes prior to probe injection. Fluorescent intensity as photons per second per centimeter square per steradian ($p/s/cm^2/sr$) was recorded from living mice, (data not shown). Images were taken at various time points (e.g., 1 min., 5 hrs. and 22 hrs.) after probe injection using an IVIS 200 imaging system equipped with a Cy5.5 filter. A rapid decrease in signal was observed from the control probe, suggesting that the signal observed for GB123 at later time points is due to modification of target proteases, resulting in retention of observable signal for at least 22 hrs. After 1 min., MDA-MB-231 injected mice showed fluorescence with both GB123 and GB125. After 5 hrs., MDA-MB 231 mice injected with GB 125 showed no fluorescence. After 22 hrs., C2C12/ras mice tumors showed higher fluorescence than MDA-MB-231 tumors.

Other protocols are known and may be adapted for administration and imaging in vivo using the present compounds. Another protocol for mouse studies is given in Joyce et al. "Cathepsin cysteine proteases are effectors of invasive growth and angiogenesis during multistage tumorigenesis," Cancer Cell 5:443-452 (May 2004), at page 452.

EXAMPLE 8

Biochemical Analysis of In vivo Labeled Tumors

Figure 6B:
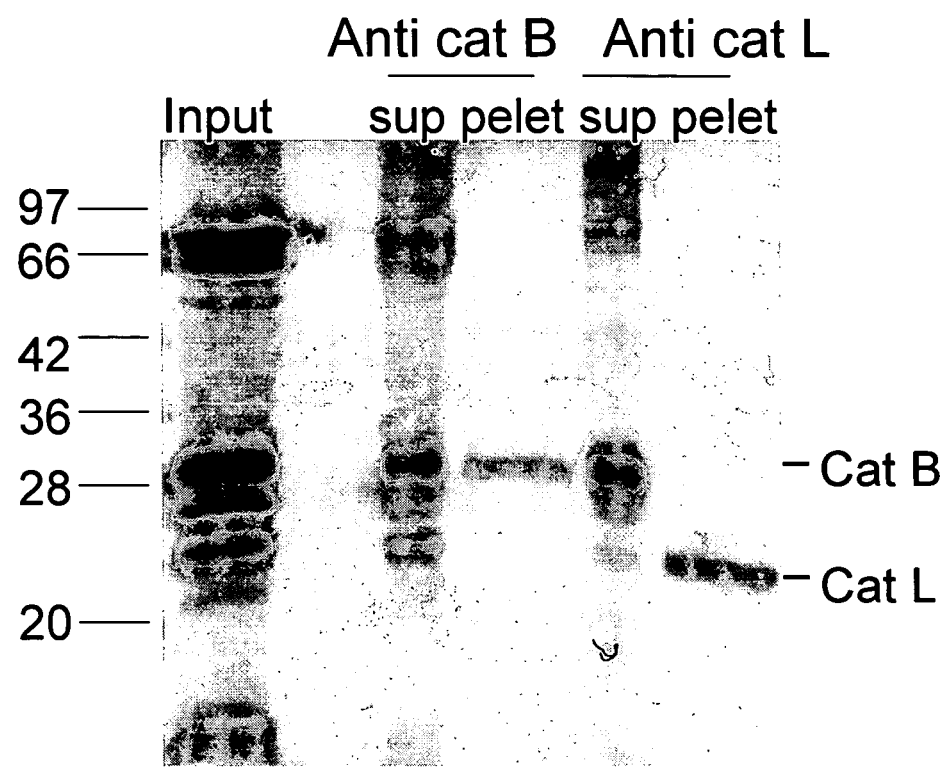
FIG. 6b is a gel showing immunoprecipitation lysates from C2/C12/ras tumor using anticathepsin B or anticathepsin L antibodies.

Tumors from mice described in Example 7 were lysed in a detergent buffer. Crude lysates were normalized for total protein, separated by SDS-PAGE, and visualized by scanning of the gel with a Typhoon flatbed laser scanner, fluorescent images of corresponding mice are shown below gel images, where spotted areas indicate fluorescent readings, as obtained in Example 7. As can be seen in FIG. 6*a*, significant fluorescence can be seen at several Mr's (relative molecular weight bands) in the GB 123 mice lysates, but not in the GB 125 (control) mouse, indicating specific labeling of several protease species. Lysates from a C2C12/ras tumor locally injected with DMSO/PBS were immuno precipitated using anti cathepsin B or cathepsin L antibodies as indicated. Samples were separated by SDS-PAGE, and visualized by scanning of the gel with a Typhoon flatbed laser scanner, as shown in FIG. 6*b*. The antibodies precipitated cat B and cat L complexes, indicating specific labeling of these proteases.

EXAMPLE 9

Ex Vivo Imaging of Tumor Tissues of Mice Injected with GB123 and GB125

Tumors from mice injected with either GB123 or GB125 were extracted 24 hours after probe injection and molded in OCT placed in tert-butanol cooled with liquid nitrogen. Cryo-sections (10 µm) of tumors were mounted with Fluoromount and imaged using a Zeiss 200M fluorescent microscope using a 40× lens and a Cy5 filter. Both merged images of bright light field and Cy5 channel and Cy5 channel showed accumulation of the specific fluorescent signal only in tissues from mice treated with the active probe GB123.

EXAMPLE 10

Stability of Probes in Mouse Serum

Figure 7:
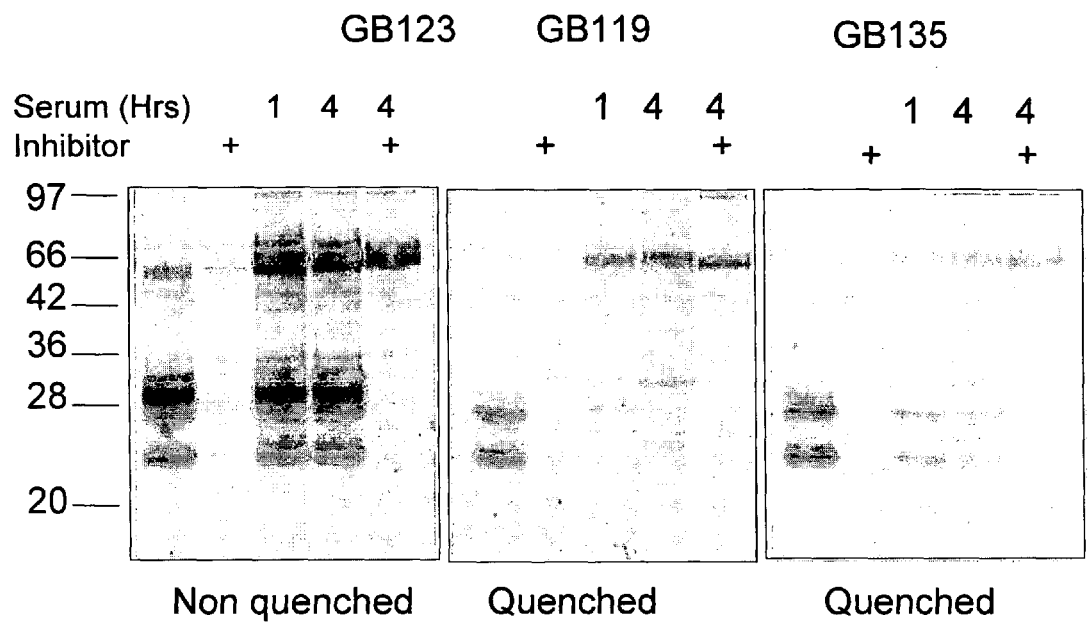
FIG. 7 is a series of photographs of three gels showing labeling by probes incubated with mouse serum, probes being GB 123 (left panel), GB 119 (middle panel) and GB 135 (right panel)

Cultures of C2C12/ras myoblast were either pre-treated with the general papain family protease inhibitor JPM-OEt (50 µM) or with control DMSO (0.1%) for one hour, then labeled by addition of 1 µM indicated probes to growth media for three hours. Probes were either incubated in mouse serum for 1 or 4 hours or not prior to addition to cells. Equal protein from crude detergent lysates were separated by SDS-PAGE, and visualized by scanning of the gel with a Typhoon flatbed laser scanner. As shown in FIG. 7, labeling was lost after pretreatment of GB119 with mouse serum, suggesting it is not stable in serum (middle panel, lanes "1" and "4"). The general non-quenched probe GB 123 and the modified quenched probe GB135 showed similar labeling even after pre-treatment with mouse serum suggesting they are likely to be stable in vivo. We have also obtained stability data for the quenched probe GB 126 showing that it is stable after 4 hrs in mouse serum, making this probe also suitable for in vivo fluorescent labeling of proteases and protease-rich sites, such as tumors.

In summary, we have found that by combining the quenched probe with the new spectral imager technology, that it is possible to image cathepsin activity in live animals using an activity-based probe. A possible further improvement would be the modification of the quenched probe to include a fluorescent tag in the far-red region, which further diminishes background fluorescence and enhances tissue penetration of light.

EXAMPLE 11

Synthesis of ABPs with Different Linkers

Figure 9:
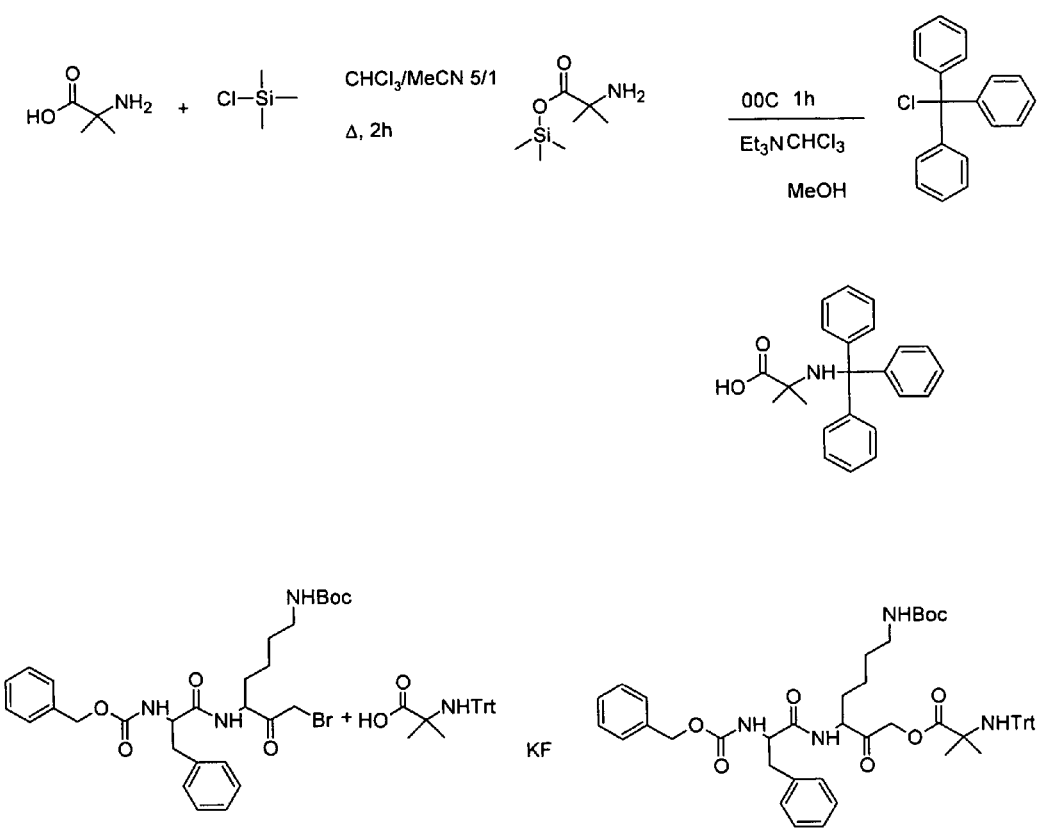
FIG. 9 is a reaction scheme showing synthesis of an ABP having an isobutyl linker, e.g. GB 135.

The linkers between the fluorophore and quencher (if present) have been found to be important to stability of the ABP in vivo, as demonstrated by the serum studies shown in FIG. 7. In this example, synthesis of linkers to the AOMK group are set forth. Referring now to FIGS. 8 and 9, the following syntheses were carried out:

Synthesis of Acid linker-QSY 7,
N-(4-QSY7-butyl)-2,6-dimethyl-terephthalamic acid Commercial 2,6 dimethylterephalic acid (0.26 mmol), HOBt (0.26 mmol, 1 eq), PyBOP, (0.29 mmol, 1.1 eq) and DIEA (1.56 mmol, 6 eq) were dissolved in DMF and stirred for 15 minutes. N-Boc-1,4-diamino butane (0.26 mmol, 1 eq) was added, pH was measured to be pH=9. After 2.5 hours reaction was acidified by addition of 1 M aqueous KHSO4, and the mixture was extracted with ethyl acetate. Subsequently, the resulting organic phase was washed with water and brine. The organic phase was dried over MgSO$_4$ and solvent removed in vacuo. Crude N-(4-Boc-butyl)-2,6-dimethyl-terephthalamic acid was purified by C18 reverse phase HPLC using a water-acetonitrile gradient. Product was eluted with 30% acetonitrile to obtain 0.094 mmol white powder, 38% yield. The Boc was removed by reaction with 25% TFA in CH$_2$Cl$_2$ (0.5 ml) for 30 minutes. The solvent was removed by co-evaporation with toluene to yield the free amine product.

A solution of 0.05 mg/µl QSY 7 succinimidyl ester (6.32 µmol, 1.05 eq) in DMSO and DIEA (19 µmol, 5 eq) were incubated with the crude amine for 1 hour. Solvent was removed with vacuo to obtain a purple solid that migrated as a single peak by LC/MS. Crude N-(4-QSY7-butyl)-2,6-dimethyl-terephthalamic acid was used in subsequent steps without further purification.

Synthesis of acyloxymethyl ketone GB136(Boc),
ZFK(Boc)-N-(4-QSY7-butyl)-2,6-dimethyl-terephtalamoyl acyloxymethyl ketone N-(4-QSY7-butyl)-2,6-dimethyl-terephthalamic acid (6.04 µmol), ZFK(Boc)BMK (25.6 µM, 4 eq) and KF (60.3 µmol, 10 eq) were dissolved in dry DMF under argon and stirred for three hour. Crude ZFK(Boc)-N-(4-QSY7-butyl)-2,6-dimethyl-terephtalamoyl acyloxymethyl ketone was purified by C18 reverse phase HPLC using water-acetonitrile gradient. Product was eluted with 70% acetonitrile to obtain 5.72 µmol purple powder, 94.6% yield.

BODIPY TMR-X Labeling of GB136

GB136 was synthesized similarly to GB117 and GB111 using 5.7 µmol GB136(Boc), (ZFK(Boc)-N-(4-QSY7-butyl)-2,6-dimethyl-benzoiyl acyloxymethyl ketone), 5.71 µmol BODIPY TMR-X succinimidyl ester and DIEA (28.6 µmol, 5 eq). GB136 was purified by HPLC and eluted with 67% acetonitrile to obtain 2.35 µmol purple powder, 41% yield.

GB135

Trityl protection of amino isobutyric acid (Aib) was performed similarly to as reported in J. Org. Chem., Vol. 67, No 4, 2002 1045-56. A stirred suspension of 10 mmol amino isobutyric acid in CHCl$_3$/MeCN (5/1) was added to chlorotrimethylsilan (10 mmol) and refluxed for 2 hours. Reaction was cooled to 0° C. and triethylamine was added dropwise (20.0 mmol, 2 eq) followed by a solution of trityl chloride in chloroform (10.0 mmol). The mixture was stirred for 1 h and methanol (2 ml) was added. Mixture was concentrated and worked up using diethyl ether/water. The water layer was washed with ether twice and combined ether layers were dried with MgSO$_4$. The crude product was used for subsequent steps without further purification.

Synthesis of ZFK(Boc)-N-Trityl Aib AOMK and
ZFK(Boc)-Aib QSY21 AOMK

ZFK(Boc)-N-Trityl Aib AOMK was obtained using a similar procedure as described for compound 4 (Example 1, FIG. 4), except using crude N-trityl protected Aib instead of N-Trityl glycine. The trityl was then removed from the crude ZFK(Boc)-N-Trityl Aib AOMK by addition of 1% TFA in CH$_2$Cl$_2$ and ZFK(Boc)-NH-Aib AOMK was purified by C18 reverse phase HPLC using water-acetonitrile gradient. Product was eluted with 40% acetonitrile to obtain 29.8 µmol white powder, 50% yield. A solution of 0.05 mg/µl QSY 21 succinimidyl ester (6.13 µmol, 1.0 eq) in DMSO and DIEA (19 µmol, 5 eq) were incubated with the crude amine for 5 hour. ZFK(Boc)-Aib QSY21 AOMK was purified using C18 reverse phase HPLC using water-acetonitrile gradient. Product was eluted with 50% acetonitrile to obtain 0.46 µmol dark blue powder, 7.5% yield.

Cy 5 Labeling of GB135, ZFK(Cy5)-Aib QSY21

ZFK(NH$_2$)-Aib QSY21 AOMK was obtained by removing the Boc from ZFK(Boc)-Aib QSY21 AOMK. The Boc was removed by addition of 25% TFA in CH$_2$Cl$_2$ (0.5 ml) to ZFK(Boc)-Aib QSY21 AOMK (0.46 µmol) for 30 minutes. The solvent was removed by co-evaporation with toluene to yield the free amine product. A DMSO solution of 0.05 mg/μl Cy 5 (0.56 μmol, 1.2 eq) was incubated with the crude ZFK (NH$_2$)-Aib QSY21 AOMK and DIEA (25 μmol, 5 eq) for 1 hour. GB135 was purified by C18 reverse phase HPLC using water-acetonitrile gradient. Product was eluted with 67% acetonitrile to obtain 0.1 μmol dark blue powder, 22% yield.

CONCLUSION

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the filed. Such patens or publications are hereby incorporated by reference to the same extent as if each was specifically and individually incorporated by reference and for the purpose of describing and enabling the method or material referred to.

REFERENCES

1. Puente, X. S., Sâanchez, L. M., Overall, C. M. & Lâopez-Otâin, C. Human and mouse proteases: a comparative genomic approach. *Nat Rev Genet* 4, 544-58 (2003).
2. Baruch, A., Jeffery, D. A. & Bogyo, M. Enzyme activity—it's all about image. *Trends Cell Biol* 14, 29-35 (2004).
3. Berger, A. B., Vitorino, P. M. & Bogyo, M. Activity-based protein profiling: applications to biomarker discovery, in vivo imaging and drug discovery. *Am J Pharmacogenomics* 4, 371-81 (2004).
4. Speers, A. E. & Cravatt, B. F. Chemical strategies for activity-based proteomics. *Chembiochem* 5, 41-7 (2004).
5. Jeffery, D. A. & Bogyo, M. Chemical proteomics and its application to drug discovery. *Curr Opin Biotechnol* 14, 87-95 (2003).
6. Adam, G. C., Sorensen, E. J. & Cravatt, B. F. Chemical strategies for functional proteomics. *Mol Cell Proteomics* 1, 781-90 (2002).
7. Jessani, N. & Cravatt, B. F. The development and application of methods for activity-based protein profiling. *Curr Opin Chem Biol* 8, 54-9 (2004).
8. Liu, Y., Patricelli, M. P. & Cravatt, B. F. Activity-based protein profiling: the serine hydrolases. *Proc Natl Acad Sci USA* 96, 14694-9 (1999).
9. Kato, D. et al. Activity-based probes that target diverse cysteine protease families. *Nat Chem Bio* in press (2005).
10. Bogyo, M., Shin, S., McMaster, J. S. & Ploegh, H. L. Substrate binding and sequence preference of the proteasome revealed by active-site-directed affinity probes. *Chem Biol* 5, 307-20 (1998).
11. Bogyo, M., Verhelst, S., Bellingard-Dubouchaud, V., Toba, S. & Greenbaum, D. Selective targeting of lysosomal cysteine proteases with radiolabeled electrophilic substrate analogs. *Chem Biol* 7, 27-38 (2000).
12. Saghatelian, A., Jessani, N., Joseph, A., Humphrey, M. & Cravatt, B. F. Activity-based probes for the proteomic profiling of metalloproteases. *Proc Natl Acad Sci USA* 101, 10000-5 (2004).
13. Chan, E. W., Chattopadhaya, S., Panicker, R. C., Huang, X. & Yao, S. Q. Developing photoactive affinity probes for proteomic profiling: hydroxamate-based probes for metalloproteases. *J Am Chem Soc* 126, 14435-46 (2004).
14. Greenbaum, D., Medzihradszky, K. F., Burlingame, A. & Bogyo, M. Epoxide electrophiles as activity-dependent cysteine protease profiling and discovery tools. *Chem Biol* 7, 569-81 (2000).
15. Greenbaum, D. et al. Chemical approaches for functionally probing the proteome. *Mol Cell Proteomics* 1, 60-8 (2002).
16. Falgueyret, J. P. et al. An activity-based probe for the determination of cysteine cathepsin protease activities in whole cells. *Anal Biochem* 335, 218-27 (2004).
17. Hemelaar, J. et al. Specific and covalent targeting of conjugating and deconjugating enzymes of ubiquitin-like proteins. *Mol Cell Biol* 24, 84-95 (2004).
18. Borodovsky, A. et al. A novel active site-directed probe specific for deubiquitylating enzymes reveals proteasome association of USP14. *Embo J* 20, 5187-96 (2001).
19. Borodovsky, A. et al. Small-molecule inhibitors and probes for ubiquitin- and ubiquitin-like-specific proteases. *Chembiochem* 6, 287-91 (2005).
20. Greenbaum, D. C. et al. A role for the protease falcipain 1 in host cell invasion by the human malaria parasite. *Science* 298, 2002-6 (2002).
21. Yasothomsrikul, S. et al. Cathepsin L in secretory vesicles functions as a prohormone-processing enzyme for production of the enkephalin peptide neurotransmitter. *Proc Natl Acad Sci USA* 100, 9590-5 (2003).
22. Goulet, B. et al. A cathepsin L isoform that is devoid of a signal peptide localizes to the nucleus in S phase and processes the CDP/Cux transcription factor. *Mol Cell* 14, 207-19 (2004).
23. Baruch, A. et al. Defining a link between gap junction communication, proteolysis, and cataract formation. *J Biol Chem* 276, 28999-9006 (2001).
24. Mahrus, S. & Craik, C. S. Selective chemical functional probes of granzymes A and B reveal granzyme B is a major effector of natural killer cell-mediated lysis of target cells. *Chem Biol* 12, 567-77 (2005).
25. Jessani, N., Liu, Y., Humphrey, M. & Cravatt, B. F. Enzyme activity profiles of the secreted and membrane proteome that depict cancer cell invasiveness. *Proc Natl Acad Sci USA* 99, 10335-40 (2002).
26. Jessani, N. et al. Carcinoma and stromal enzyme activity profiles associated with breast tumor growth in vivo. *Proc Natl Acad Sci USA* 101, 13756-61 (2004).
27. Joyce, J. A. et al. Cathepsin cysteine proteases are effectors of invasive growth and angiogenesis during multistage tumorigenesis. *Cancer Cell* 5, 443-53 (2004).
28. Okerberg, E. S. et al. High-resolution functional proteomics by active-site peptide profiling. *Proc Natl Acad Sci USA* 102, 4996-5001 (2005).
29. Powers, J. C., Asgian, J. L., Ekici, O. D. & James, K. E. Irreversible inhibitors of serine, cysteine, and threonine proteases. *Chem Rev* 102, 4639-750 (2002).
30. Sando, S. & Kool, E. T. Quencher as leaving group: efficient detection of DNA-joining reactions. *J Am Chem Soc* 124, 2096-7 (2002).
31. Sando, S. & Kool, E. T. Imaging of RNA in bacteria with self-ligating quenched probes. *J Am Chem Soc* 124, 9686-7 (2002).
32. Turk, D., Guncar, G., Podobnik, M. & Turk, B. Revised definition of substrate binding sites of papain-like cysteine proteases. *Biol Chem* 379, 137-47 (1998).
33. Musil, D. et al. The refined 2.15 A X-ray crystal structure of human liver cathepsin B: the structural basis for its specificity. *Embo J* 10, 2321-30 (1991).
34. O'Brien, L. E., Zegers, M. M. & Mostov, K. E. Opinion: Building epithelial architecture: insights from three-dimensional culture models. *Nat Rev Mol Cell Biol* 3, 531-7 (2002).
35. Debnath, J., Muthuswamy, S. K. & Brugge, J. S. Morphogenesis and oncogenesis of MCF-10A mammary epithelial acini grown in three-dimensional basement membrane cultures. *Methods* 30, 256-68 (2003).
36. Bieth, J. G. Theoretical and practical aspects of proteinase inhibition kinetics. *Methods Enzymol* 248, 59-84 (1995).
37. Barlic-Maganja, D., Dolinar, M. & Turk, V. The influence of Ala205 on the specificity of cathepsin L produced by dextran sulfate assisted activation of the recombinant proenzyme. *Biol Chem* 379, 1449-52 (1998).
38. Deval, C., Bechet, D., Obled, A. & Ferrara, M. Purification and properties of different isoforms of bovine cathepsin B. *Biochem Cell Biol* 68, 822-6 (1990).
39. Moin, K. et al. Human tumour cathepsin B. Comparison with normal liver cathepsin B. *Biochem J* 285, 427-34 (1992).

What is claimed is:

1. An activity based probe for labeling an active protease, having the formula

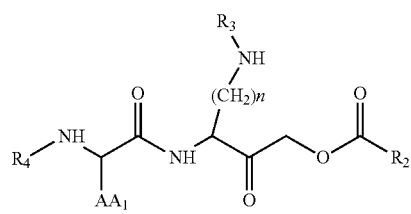

Formula I where
(a) $AA_1$ is a phenylalanine side chain;
(b) n is four;
(c) $R_2$ is a QSY® quencher, wherein the quencher is linked through a lower alkyl, aryl or lower alkyl-aryl linker;
(d) $R_3$ is a cyanine dye and a lower alkyl; and
(e) $R_4$ is a capping group selected from the group consisting of aliphatic ester, aromatic ester or heterocyclic ester.

2. A compound having the formula:

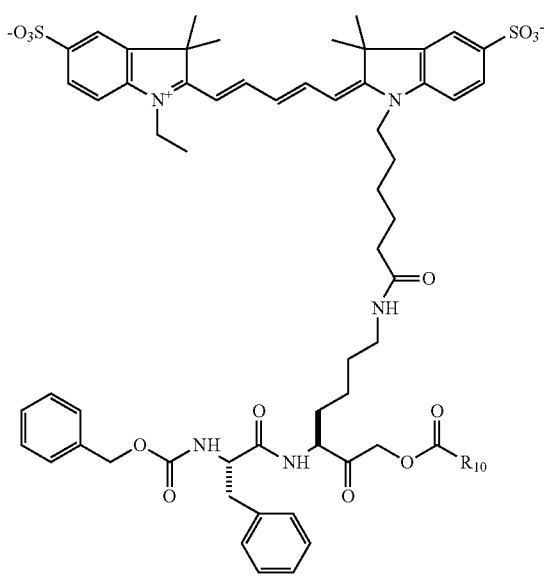

where R10 has the formula below where * indicates a point of attachment:

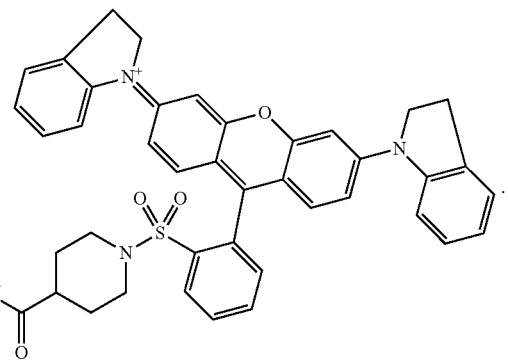

3. A compound having the formula:

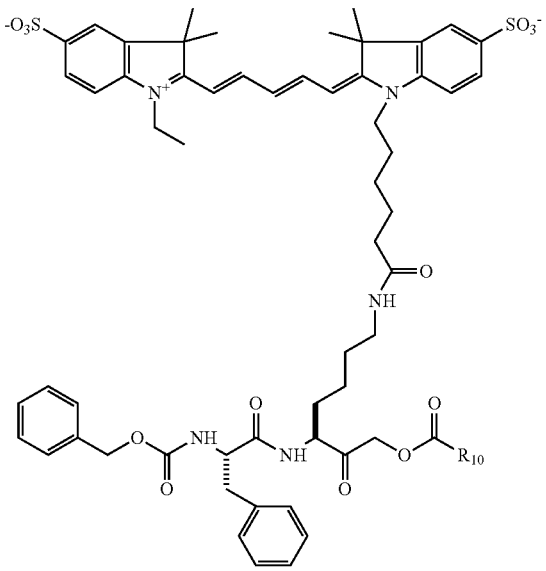

where $R_{10}$ has the formula:

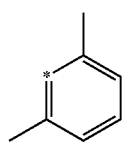

in which * indicates a point of attachment.

* * * * *

UNITED STATES PATENT AND TRADEMARK OFFICE
CERTIFICATE OF CORRECTION

PATENT NO. : 8,968,700 B2
APPLICATION NO. : 11/502255
DATED : March 3, 2015
INVENTOR(S) : Bogyo et al.

Page 1 of 1

It is certified that error appears in the above-identified patent and that said Letters Patent is hereby corrected as shown below:

In the specification

Please replace Column 1, lines 11-16 with:

--STATEMENT OF GOVERNMENT SUPPORT

This invention was made with Government support under contract RR020843 awarded by the National Institutes of Health. The Government has certain rights in the invention.--

Signed and Sealed this
Twenty-third Day of August, 2016

Michelle K. Lee
*Director of the United States Patent and Trademark Office*